(12) United States Patent
Zemlok et al.

(10) Patent No.: US 10,653,416 B2
(45) Date of Patent: *May 19, 2020

(54) POWERED SURGICAL INSTRUMENT

(71) Applicant: Covidien LP, Mansfield, MA (US)

(72) Inventors: Michael A. Zemlok, Prospect, CT (US); David Racenet, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/523,387

(22) Filed: Jul. 26, 2019

(65) Prior Publication Data

US 2019/0343517 A1    Nov. 14, 2019

Related U.S. Application Data

(63) Continuation of application No. 15/151,625, filed on May 11, 2016, which is a continuation of application
(Continued)

(51) Int. Cl.
*A61B 17/068* (2006.01)
*A61B 17/072* (2006.01)
(Continued)

(52) U.S. Cl.
CPC .......... *A61B 17/068* (2013.01); *A61B 17/072* (2013.01); *A61B 17/07207* (2013.01); *A61B 17/115* (2013.01); *A61B 17/1114* (2013.01); *A61B 17/1155* (2013.01); *A61B 2017/00017* (2013.01); *A61B 2017/00199* (2013.01); *A61B 2017/00398* (2013.01); *A61B 2017/00464* (2013.01); *A61B 2017/00473* (2013.01); *A61B 2017/00482* (2013.01);
(Continued)

(58) Field of Classification Search
CPC .. A61B 17/072; A61B 17/1114; A61B 17/115
USPC ............ 227/175.1–180.1; 606/153, 149, 205
See application file for complete search history.

(56) References Cited

U.S. PATENT DOCUMENTS

| 37,165 A | 12/1862 | Gary |
| 3,209,754 A | 10/1965 | Brown |

(Continued)

FOREIGN PATENT DOCUMENTS

| CN | 1636526 A | 7/2005 |
| CN | 1665449 A | 9/2005 |

(Continued)

OTHER PUBLICATIONS

Australian Office Action corresponding to counterpart Int'l Appln. No. AU 2015204308, dated May 18, 2016.
(Continued)

*Primary Examiner* — Nathaniel C Chukwurah
(74) *Attorney, Agent, or Firm* — Carter, DeLuca & Farrell LLP

(57) ABSTRACT

A surgical instrument including a housing, an endoscopic portion, a shaft portion and an end effector is disclosed. The endoscopic portion extends distally from the housing and defines a longitudinal axis. The shaft portion is selectively connectable to a distal end of the endoscopic portion. The end effector is selectively connectable to a distal end of the shaft portion.

20 Claims, 20 Drawing Sheets

Related U.S. Application Data

No. 11/894,959, filed on Aug. 21, 2007, now abandoned, which is a continuation-in-part of application No. 11/786,934, filed on Apr. 13, 2007, now Pat. No. 7,950,560.

(51) Int. Cl.
*A61B 17/115* (2006.01)
*A61B 17/11* (2006.01)
*A61B 17/00* (2006.01)
*A61B 17/29* (2006.01)

(52) U.S. Cl.
CPC ............ *A61B 2017/00734* (2013.01); *A61B 2017/07278* (2013.01); *A61B 2017/2905* (2013.01); *A61B 2017/2927* (2013.01); *A61B 2017/2943* (2013.01)

(56) References Cited

U.S. PATENT DOCUMENTS

| | | |
|---|---|---|
| 3,273,562 A | 9/1966 | Brown |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,304,236 A | 12/1981 | Conte et al. |
| 4,331,277 A | 5/1982 | Green |
| 4,383,634 A | 5/1983 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,520,817 A | 6/1985 | Green |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,805,617 A | 2/1989 | Bedi et al. |
| 4,807,628 A | 2/1989 | Peters et al. |
| 4,852,558 A | 8/1989 | Outerbridge |
| 4,911,148 A | 3/1990 | Sosnowski et al. |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,649,956 A | 7/1997 | Jensen et al. |
| 5,653,374 A | 8/1997 | Young et al. |
| 5,658,300 A | 8/1997 | Bito et al. |
| 5,658,312 A | 8/1997 | Green et al. |

(56) References Cited

U.S. PATENT DOCUMENTS

| | | |
|---|---|---|
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,690,675 A | 11/1997 | Sawyer et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,752,644 A | 5/1998 | Bolanos et al. |
| 5,755,726 A | 5/1998 | Pratt et al. |
| 5,759,171 A | 6/1998 | Coelho et al. |
| 5,779,130 A | 7/1998 | Alesi et al. |
| 5,782,396 A | 7/1998 | Mastri et al. |
| 5,782,397 A | 7/1998 | Koukline |
| 5,785,713 A | 7/1998 | Jobe |
| 5,788,698 A | 8/1998 | Savornin |
| 5,797,536 A | 8/1998 | Smith et al. |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,517,565 B1 | 2/2003 | Whitman et al. |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |

(56) References Cited

U.S. PATENT DOCUMENTS

| | | | |
|---|---|---|---|
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,422,136 B1 | 9/2008 | Marczyk |
| 7,431,188 B1 | 10/2008 | Marczyk |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,556,185 B2 | 7/2009 | Viola |
| 7,575,144 B2 | 8/2009 | Ortiz et al. |
| 7,743,960 B2 | 6/2010 | Whitman et al. |
| 7,823,760 B2 | 11/2010 | Zemlok et al. |
| 7,887,530 B2 | 2/2011 | Zemlok et al. |
| 7,950,560 B2 * | 5/2011 | Zemlok ............... A61B 17/068 227/175.1 |
| 8,800,837 B2 | 8/2014 | Zemlok |
| 2001/0031975 A1 | 10/2001 | Whitman et al. |
| 2002/0025891 A1 | 2/2002 | Colosky et al. |
| 2002/0103489 A1 | 8/2002 | Ku |
| 2002/0111641 A1 | 8/2002 | Peterson et al. |
| 2002/0165541 A1 | 11/2002 | Whitman |
| 2003/0009195 A1 | 1/2003 | Field et al. |
| 2003/0073981 A1 | 4/2003 | Whitman et al. |
| 2003/0114851 A1 | 6/2003 | Truckai et al. |
| 2003/0120306 A1 | 6/2003 | Burbank et al. |
| 2003/0139746 A1 | 7/2003 | Groiso |
| 2004/0094597 A1 | 5/2004 | Whitman et al. |
| 2004/0153124 A1 | 8/2004 | Whitman |
| 2004/0230221 A1 | 11/2004 | Gadberry et al. |
| 2004/0232199 A1 | 11/2004 | Shelton et al. |
| 2004/0232201 A1 | 11/2004 | Wenchell et al. |
| 2004/0249366 A1 | 12/2004 | Kunz |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006434 A1 | 1/2005 | Wales et al. |
| 2005/0010235 A1 | 1/2005 | VanDusseldorp |
| 2005/0023324 A1 | 2/2005 | Doll et al. |
| 2005/0067458 A1 | 3/2005 | Swayze et al. |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2005/0139636 A1 | 6/2005 | Schwemberger et al. |
| 2005/0145674 A1 | 7/2005 | Sonnenschein et al. |
| 2005/0177176 A1 | 8/2005 | Gerbi et al. |
| 2005/0178813 A1 | 8/2005 | Swayze et al. |
| 2005/0184125 A1 | 8/2005 | Marczyk |
| 2005/0187576 A1 | 8/2005 | Whitman et al. |
| 2005/0192609 A1 | 9/2005 | Whitman et al. |
| 2005/0220639 A1 | 10/2005 | Sasaki et al. |
| 2005/0228341 A1 | 10/2005 | Edgerley |
| 2005/0247753 A1 | 11/2005 | Kelly et al. |
| 2006/0000867 A1 | 1/2006 | Shelton et al. |
| 2006/0022014 A1 | 2/2006 | Shelton et al. |
| 2006/0022015 A1 | 2/2006 | Shelton et al. |
| 2006/0025811 A1 | 2/2006 | Shelton |
| 2006/0049229 A1 | 3/2006 | Milliman et al. |
| 2006/0097025 A1 | 5/2006 | Milliman et al. |
| 2006/0151567 A1 | 7/2006 | Roy |
| 2006/0175375 A1 | 8/2006 | Shelton et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0084896 A1 | 4/2007 | Doll et al. |
| 2007/0084897 A1 | 4/2007 | Shelton et al. |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0125826 A1 | 6/2007 | Shelton |
| 2007/0152014 A1 | 7/2007 | Gillum et al. |
| 2007/0158385 A1 | 7/2007 | Hueil et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175961 A1 | 8/2007 | Shelton et al. |
| 2007/0175962 A1 | 8/2007 | Shelton et al. |

(56) References Cited

U.S. PATENT DOCUMENTS

| | | |
|---|---|---|
| 2007/0175964 A1 | 8/2007 | Shelton et al. |
| 2007/0187453 A1 | 8/2007 | Smith et al. |
| 2007/0219563 A1 | 9/2007 | Voegele |
| 2007/0265640 A1 | 11/2007 | Kortenbach et al. |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0110957 A1 | 5/2008 | McBride et al. |
| 2008/0135600 A1 | 6/2008 | Hiranuma et al. |
| 2008/0164296 A1 | 7/2008 | Shelton et al. |
| 2008/0169329 A1 | 7/2008 | Shelton et al. |
| 2008/0185419 A1 | 8/2008 | Smith et al. |
| 2008/0245842 A1 | 10/2008 | Marczyk |
| 2008/0255413 A1 | 10/2008 | Zemlok et al. |
| 2008/0255418 A1 | 10/2008 | Zemlok et al. |
| 2008/0314959 A1 | 12/2008 | Viola et al. |
| 2009/0090764 A1 | 4/2009 | Viola |
| 2009/0101692 A1 | 4/2009 | Whitman et al. |
| 2013/0324978 A1 | 12/2013 | Nicholas et al. |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 1769754 A1 | 4/2007 |
| EP | 1813203 A2 | 8/2007 |
| WO | 9729694 A1 | 8/1997 |
| WO | 9740760 A1 | 11/1997 |
| WO | 9952489 | 10/1999 |
| WO | 03026511 A1 | 4/2003 |
| WO | 03030743 A2 | 4/2003 |
| WO | 2004032760 A2 | 4/2004 |
| WO | 2007030753 A2 | 3/2007 |
| WO | 2007118179 A2 | 10/2007 |

OTHER PUBLICATIONS

European Search Report for corresponding EP 08252703dated Oct. 31, 2008 (3 pages).
European Search Report for corresponding EP 08251357 dated Sep. 29, 2009 (3 pages).
European Search Report dated Apr. 17, 2007 for Corresponding Patent Application EP06026840.
International Search Report for corresponding PCT Application—PCT/US06/21524—dated May 28, 2008 (4 Pages).
Detemple, P., "Microtechnology in Modern Health Care", Med Device Technol. 9(9):18-25 (1998).
European Search Report for corresponding EP 08252703.7 dated Oct. 31, 2008 (3 pages).
European Search Report dated Feb. 27, 2009 for Corresponding Patent Application 08253184.9.
European Search Report for corresponding EP 08252703.7 dated Oct. 31, 2008 (7 pages).
Australian Examination Report No. 1 corresponding to counterpart Int'l Appln. No. AU 2015202969 dated Jul. 25, 2016.
Chinese Second Office Action corresponding to counterpart Int'l Appln. No. CN 201410156294.7 dated Aug. 3, 2016.
European Office Action corresponding to counterpart Int'l Appln. No. EP 14 18 3666.8 dated Aug. 5, 2016.
European Office Action corresponding to counterpart Int'l Appln. No. EP 14 18 3666.8 dated May 2, 2017.
Chinese First Office Action corresponding to counterpart Chinese Application No. CN 201610197277.7 dated Dec. 15, 2017.
Australian Examination Report No. 1 corresponding to counterpart Patent Appln. AU 2016273868 dated Apr. 30, 2018.
European Office Action corresponding to counterpart Patent Appln. EP 11 17 3501.5 dated Oct. 2, 2018.

* cited by examiner

POWERED SURGICAL INSTRUMENT

CROSS REFERENCE TO RELATED APPLICATION

This application is a continuation of U.S. patent application Ser. No. 15/151,625, filed May 11, 2016, which is a continuation claiming the benefit of and priority to U.S. patent application Ser. No. 11/894,959, filed on Aug. 21, 2007, which is a Continuation-in-Part Application claiming the benefit of and priority to U.S. patent application Ser. No. 11/786,934, filed on Apr. 13, 2007, now U.S. Pat. No. 7,950,560, the entire contents of each of which are hereby incorporated by reference herein.

BACKGROUND

Technical Field

The present disclosure relates to surgical instruments for fastening body tissue and, more particularly, to a powered surgical instrument having a drive gear configured to be movable to affect rotation, articulation and actuation of the instrument.

Background of Related Art

Surgical devices wherein tissue is first grasped or clamped between opposing jaw structure and then joined by surgical fasteners are well known in the art. In some instruments, a knife is provided to cut the tissue which has been joined by the fasteners. The fasteners typically include surgical staples and two part polymeric fasteners.

Instruments for this purpose may include two elongated members which are respectively used to capture or clamp tissue. Typically, one of the members carries a staple cartridge that houses a plurality of staples arranged in rows while the other member has an anvil that defines a surface for forming the staple legs as the staples are driven from the staple cartridge. Several instruments include clamps, handles and/or knobs to affect actuation along with rotation and articulation of an end effector. Such surgical instruments can require the user to exert a significant force in operating the handles, knobs, etc., and require more than one hand to operate the instrument.

Surgical instruments with actuators that require less force to operate are desired. In addition, surgical instruments which perform multiple functions with one handed operation are also desired.

SUMMARY

The present disclosure relates to a surgical instrument including a housing, an endoscopic portion, a drive gear, a drive motor, a shift motor and an end effector. The endoscopic portion extends distally from the housing and defines a longitudinal axis. The drive gear is disposed at least partially within the housing and is rotatable about a drive gear axis which extends therethrough. The drive gear is selectively movable along the drive gear axis. The drive motor is disposed in mechanical cooperation with the drive gear and is configured to rotate the drive gear. The shift motor is disposed in mechanical cooperation with the drive gear and is configured to move the drive gear along the drive gear axis. The end effector is disposed adjacent a distal portion of the endoscopic portion.

The present disclosure also relates to a method of applying surgical fasteners to tissue. The method of this embodiment includes providing a powered surgical instrument which includes a housing, an endoscopic portion, a drive gear and an end effector. The endoscopic portion extends distally from the housing and defines a longitudinal axis. The drive gear is disposed at least partially within the housing and is rotatable about a drive gear axis extending therethrough. The drive gear is selectively movable along the drive gear axis. The end effector is disposed adjacent a distal portion of the endoscopic portion. The method further includes moving the drive gear along the drive gear axis and rotating the drive gear about the drive gear axis.

DESCRIPTION OF THE DRAWINGS

An embodiment of the presently disclosed powered surgical instrument is disclosed herein with reference to the drawings, wherein.

DETAILED DESCRIPTION OF EMBODIMENTS

Figure 1:
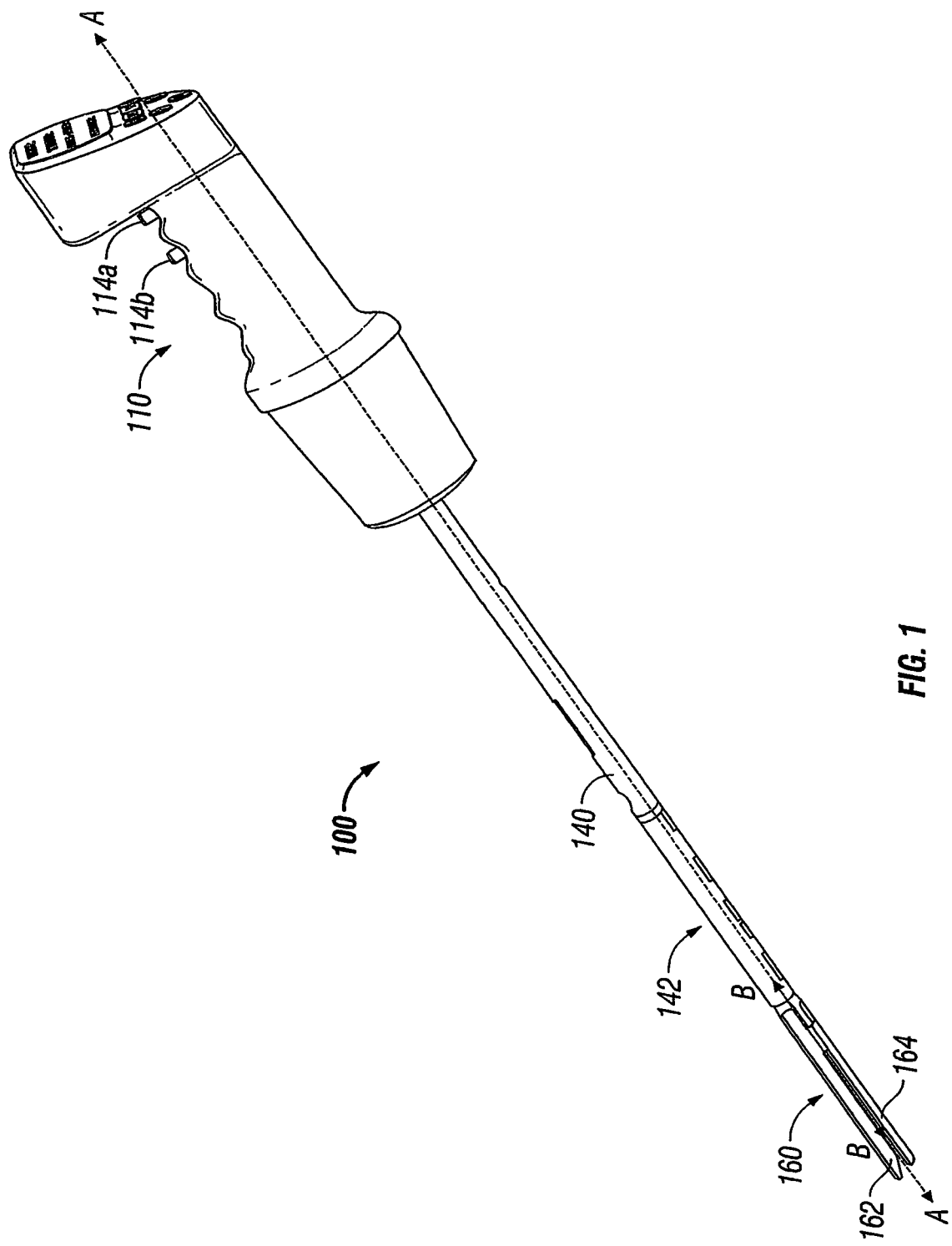
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 100. Referring initially to FIG. 1, powered surgical instrument 100 includes a housing 110, an endoscopic portion 140 defining a longitudinal axis A-A extending therethrough, and an end effector 160, defining a longitudinal axis B-B (illustrated substantially aligned with axis A-A in FIG. 1) extending therethrough. Endoscopic portion 140 extends distally from housing 110 and end effector 160 is disposed adjacent a distal portion 142 of endoscopic portion 140.

Figure 2:
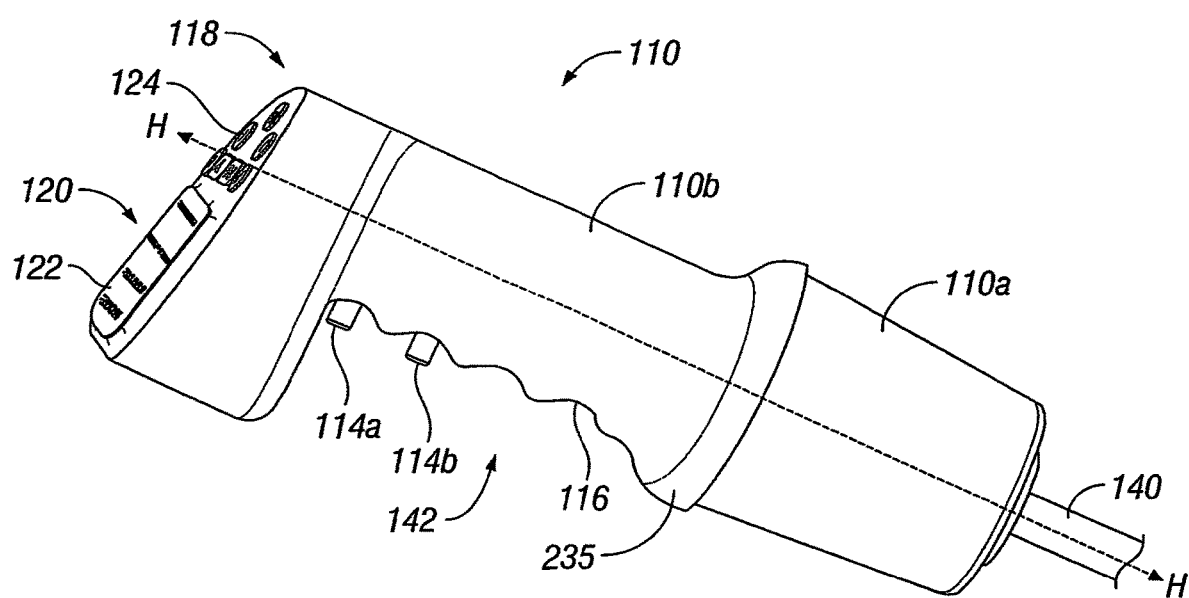
FIG. 2 is an enlarged partial perspective view of the powered surgical instrument of FIG. 1.
Figure 3:
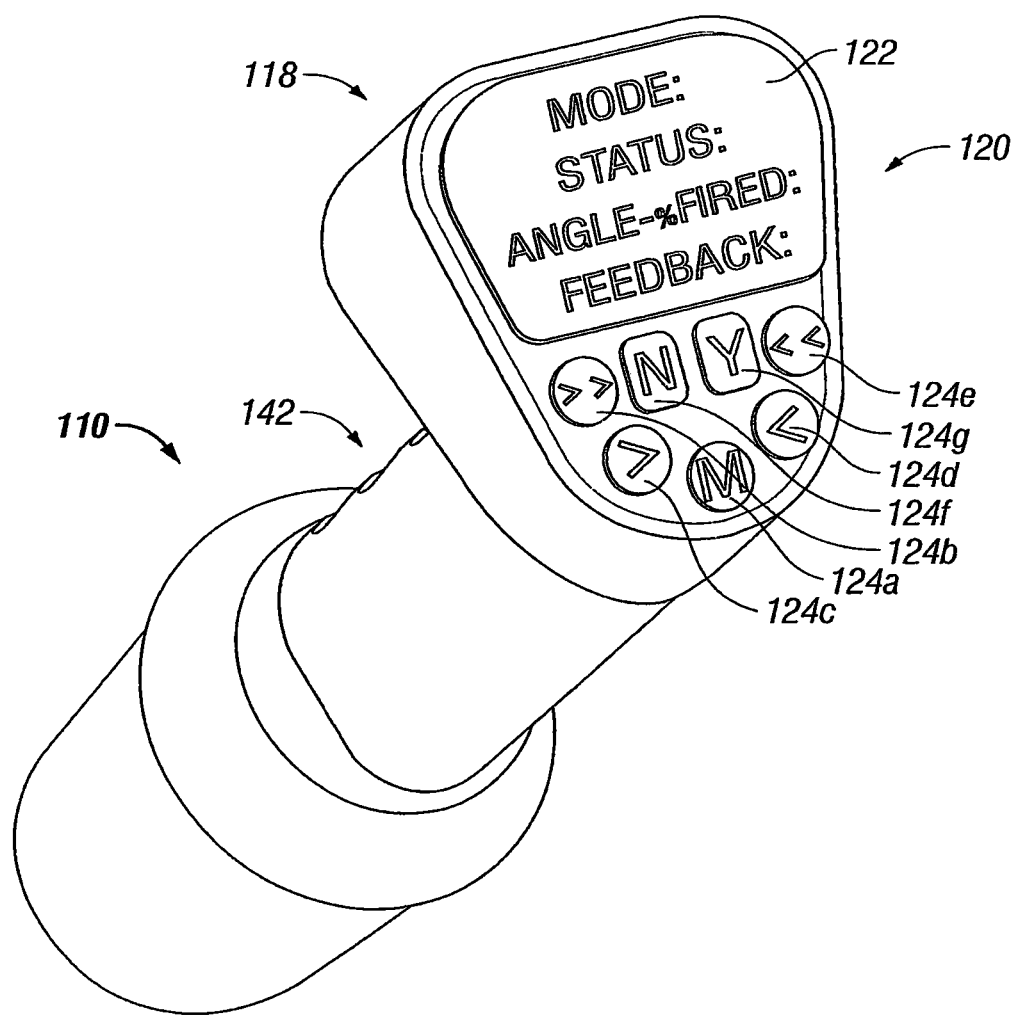
FIG. 3 is an enlarged partial perspective view of the powered surgical instrument of FIGS. 1 and 2.

With reference to FIGS. 2 and 3, an enlarged view of housing 110 is illustrated according to an embodiment of the present disclosure. In the illustrated embodiment, housing 110 includes a handle portion 112 having at least one button 114 thereon (two buttons 114a and 114b are shown). Handle portion 112, which defines a handle axis H-H, is shown having indentations 116 that correspond to fingers of a user. Each button 114a and 114b is shown as being disposed on an indentation 116 to facilitate its depression by a user's finger.

With continued reference to FIGS. 2 and 3, a proximal area 118 of housing 110 includes a user interface 120. In the illustrated embodiment, user interface 120 includes a screen 122 and at least one switch 124 (seven switches 124a-124g are shown). Screen 122 displays readable information thereon, including status information of powered surgical instrument 100 in an embodiment. Switches 124a-124g control various actions of powered surgical instrument 100, as is described in detail below.

FIGS. 4-7, 9-11 and 14 illustrate various internal components of powered surgical instrument 100, including a drive gear 200 or drive member, a drive motor 210 and a shift motor 220. It is envisioned that a three-position solenoid, for instance, can be used as an alternative to shift motor 220. Drive gear 200 is rotatable about a drive gear axis C-C extending therethrough (FIG. 4) and is selectively movable along drive gear axis C-C. Drive motor 210 is disposed in mechanical cooperation with drive gear 200 and is configured to rotate drive gear 200 about drive gear axis C-C.

Shift motor 220 is disposed in mechanical cooperation with drive gear 200 (drive motor 210 is illustrated between drive gear 200 and shift motor 220 in accordance with a disclosed embodiment) and is configured to translate drive gear 200 axially along drive gear axis C-C. In a disclosed embodiment, drive motor 210 and/or shift motor 220 may be a motor or a gear motor, which may include gearing incorporated within its housing. Shift motor 220 is configured to selectively move drive gear 200 between a plurality of positions; three positions are shown in the illustrated embodiments. The first position, illustrated in FIGS. 5 and 6, enables rotation of end effector 160; the second position, illustrated in FIG. 7, enables articulation of end effector 160; and the third position, illustrated in FIGS. 9-11 and 14, enables actuation of powered surgical instrument 100.

Figure 5:
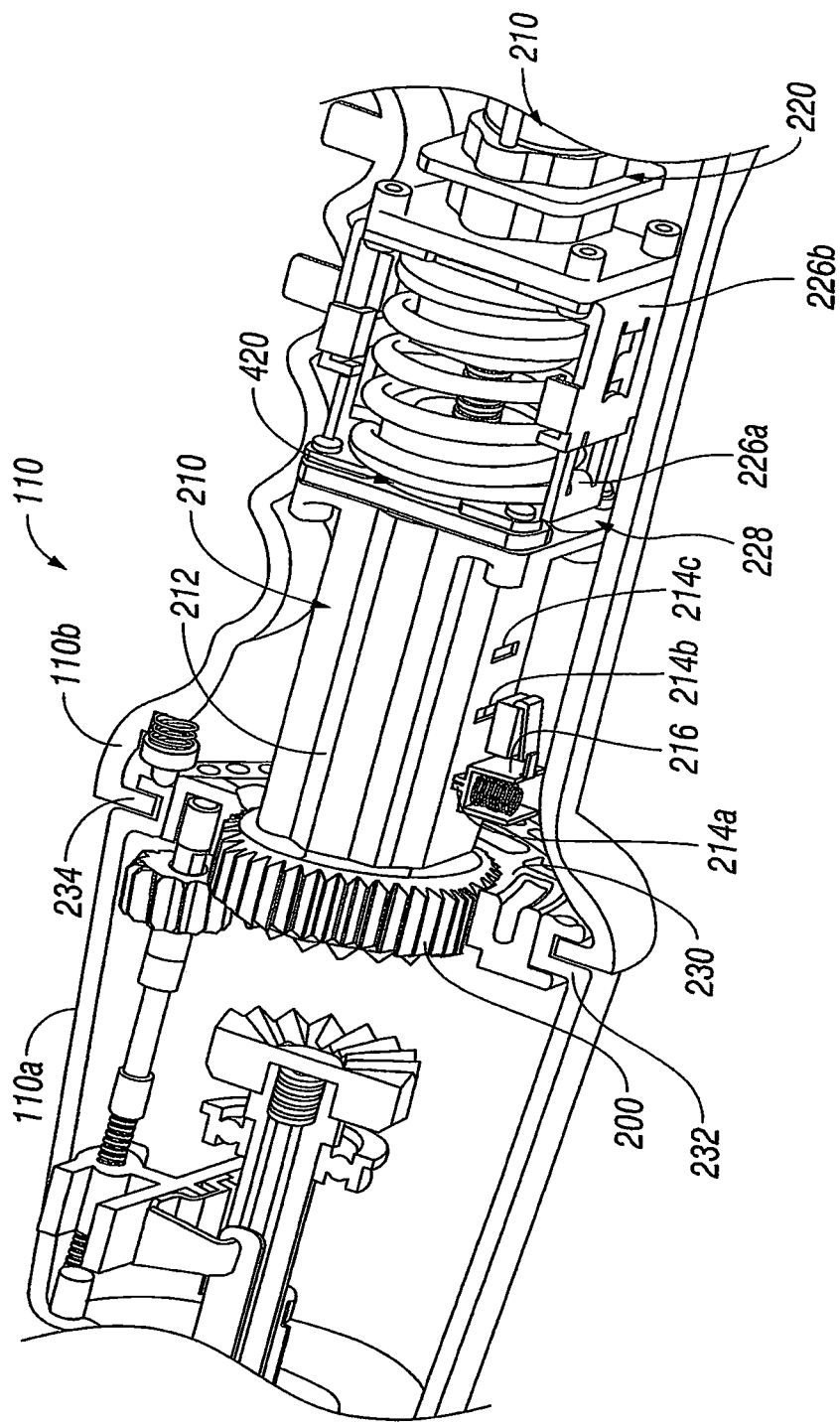
FIGS. 5 and 6 are partial perspective sectional views showing the internal components of the powered surgical instrument of FIGS. 1-4 disposed in a first position.
Figure 6:
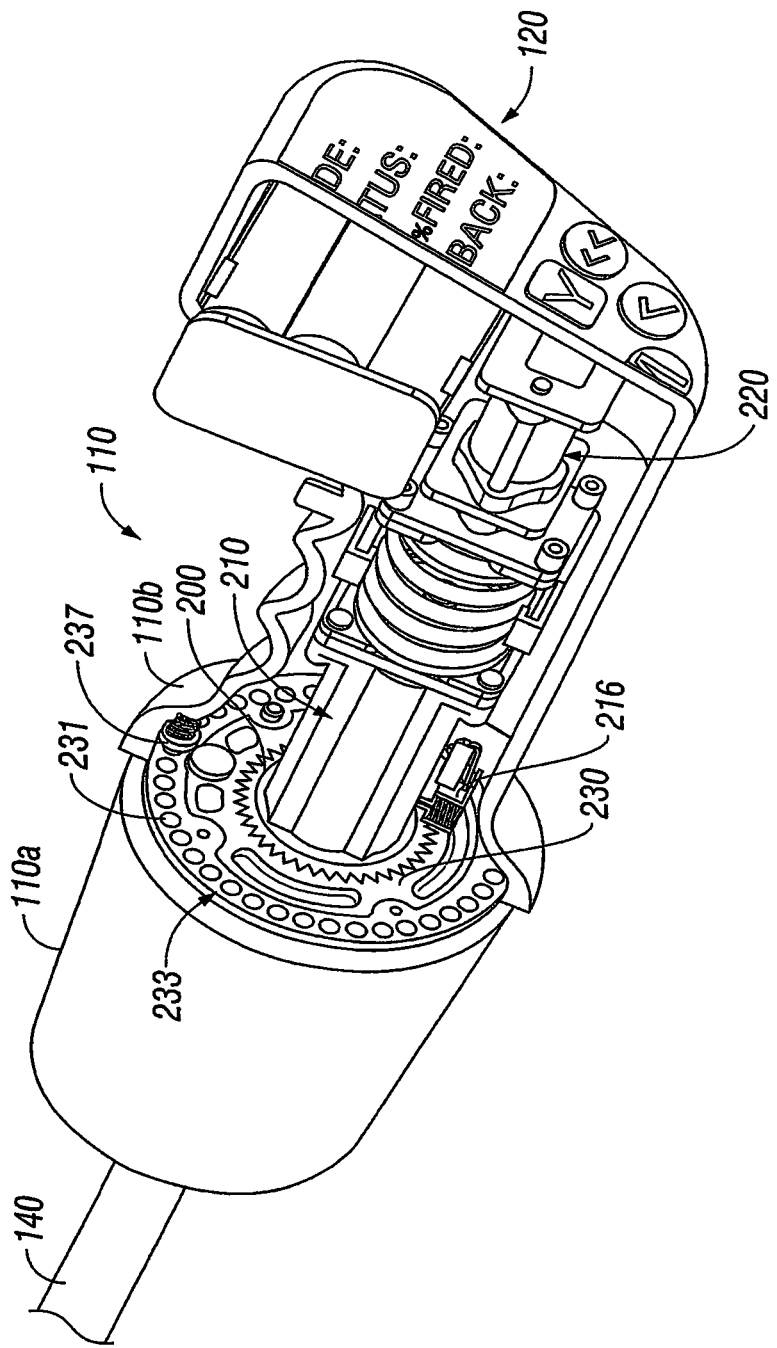
Figure 7:
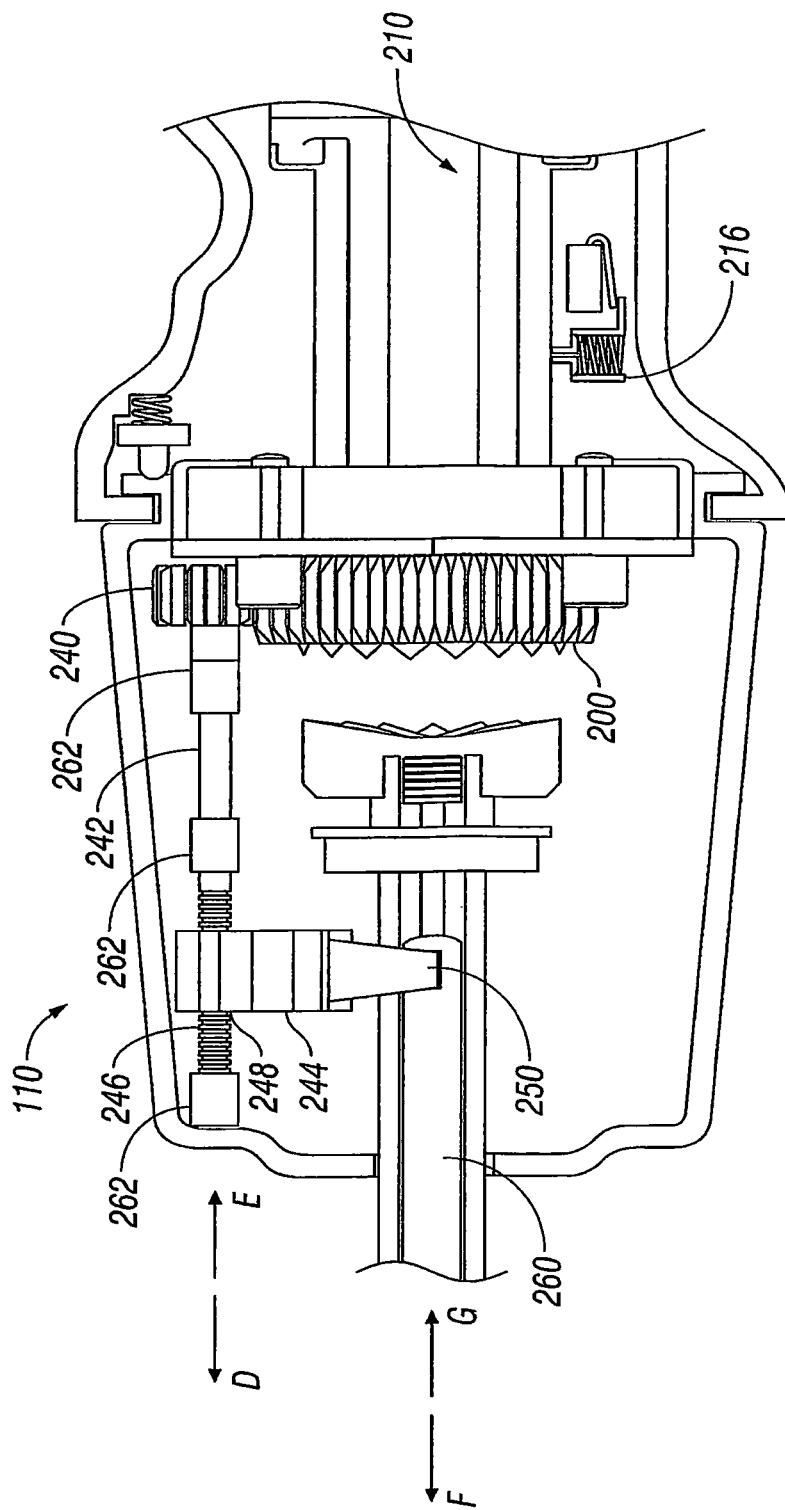
FIG. 7 is a cross-sectional view of the internal components of the powered surgical instrument of FIGS. 1-5 disposed in a second position.
Figure 9:
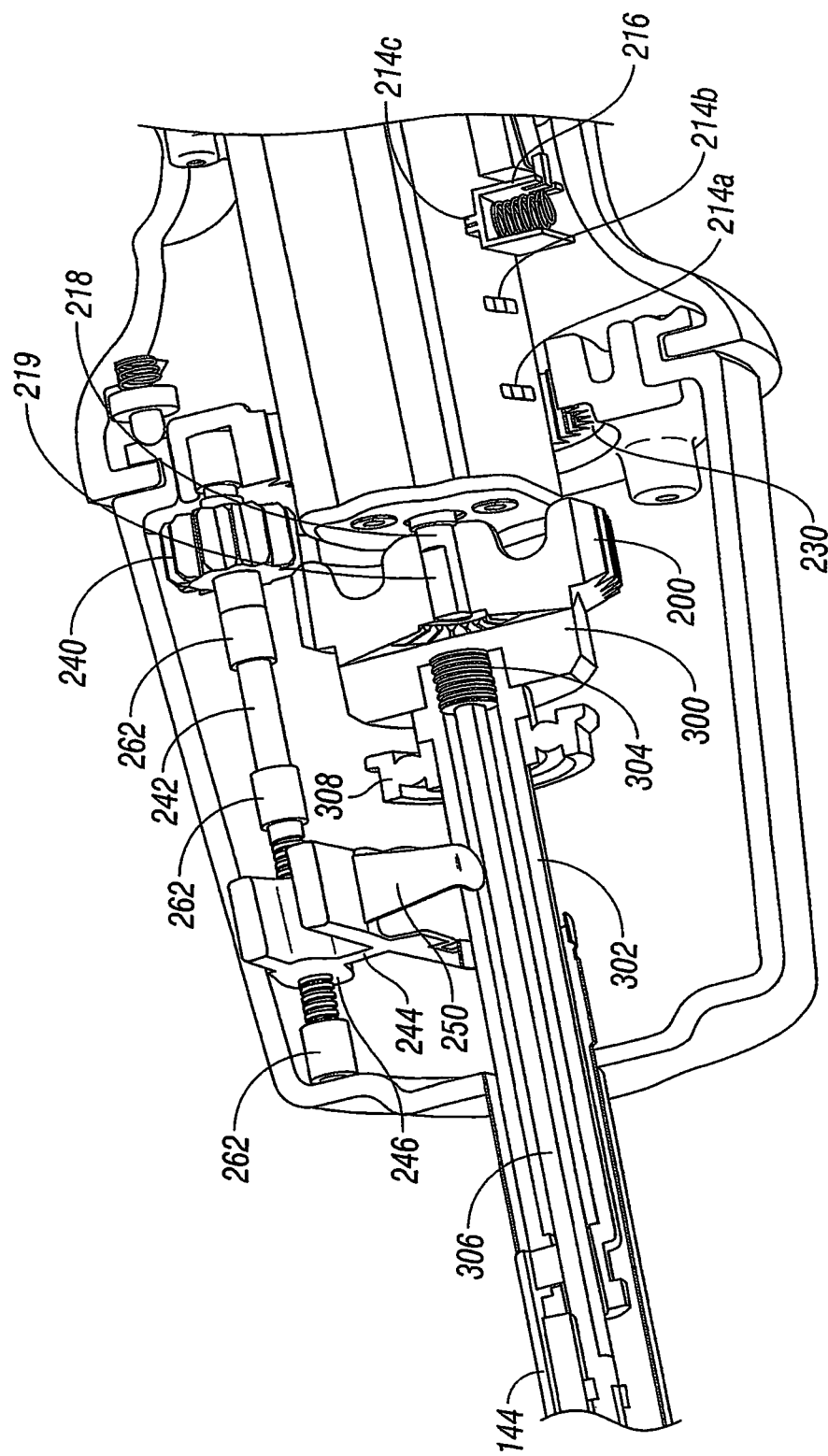
FIGS. 9-11 are partial perspective sectional views of the internal components of the powered surgical instrument of FIGS. 1-8 disposed in a third position.
Figure 10:
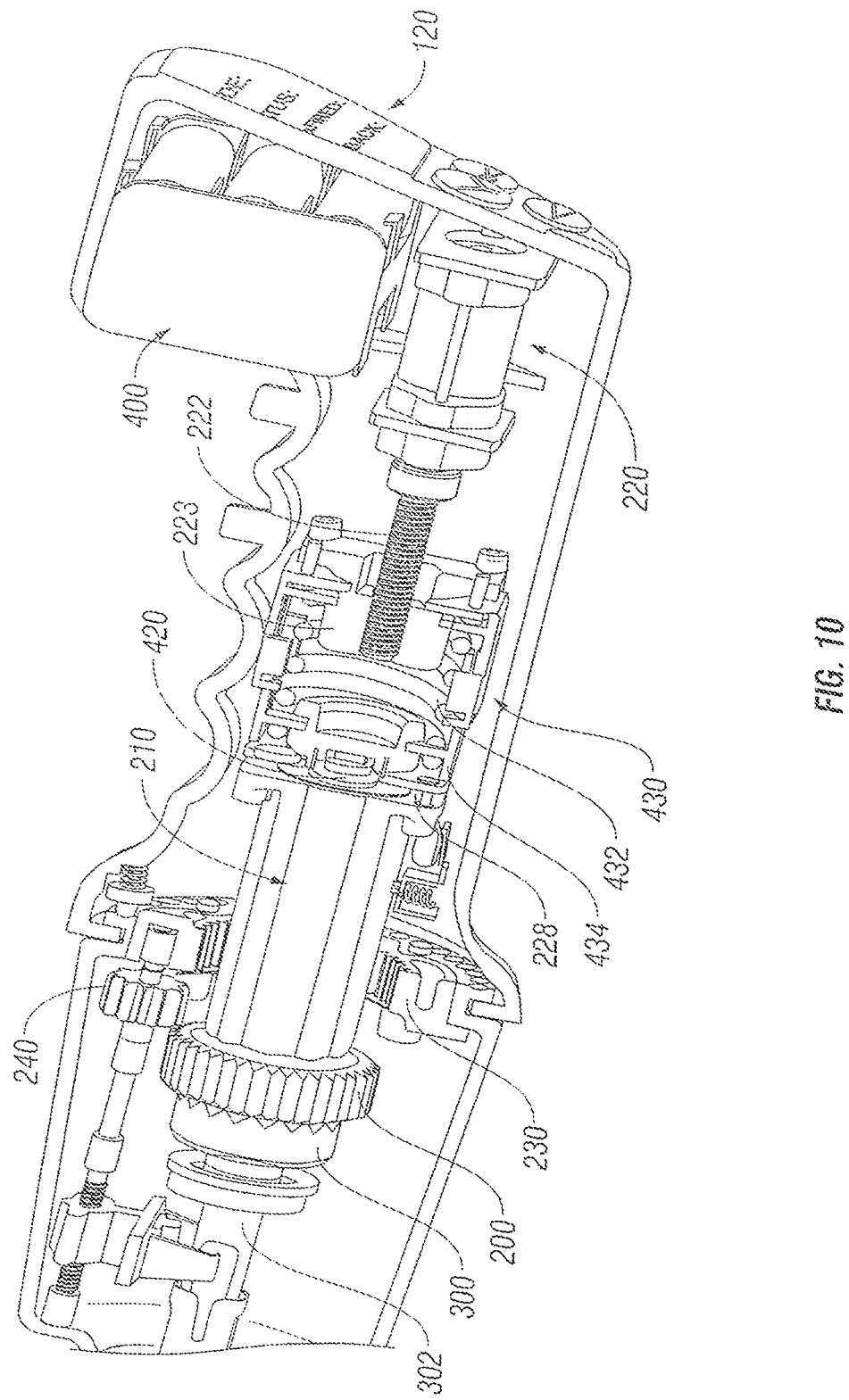
Figure 14:
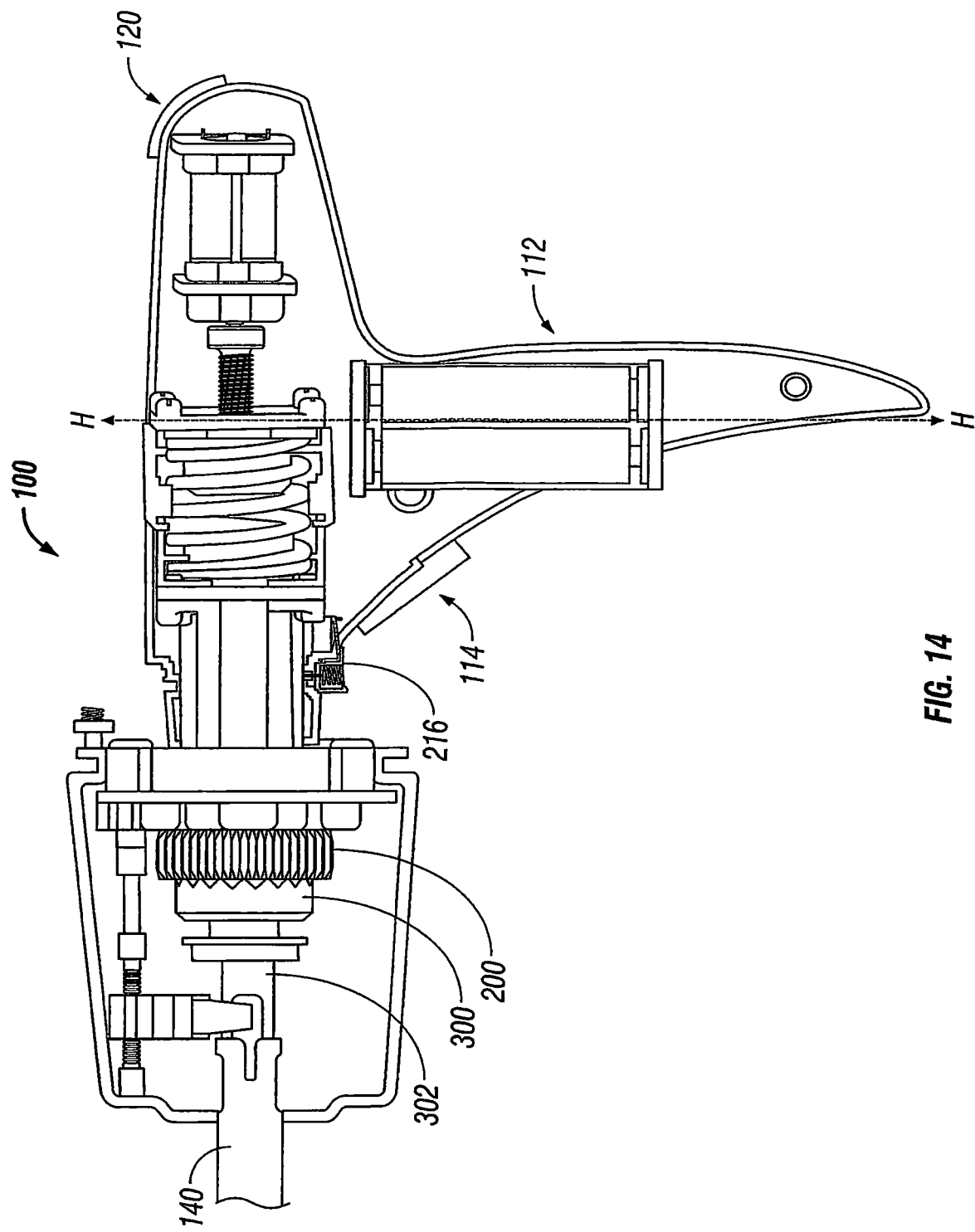
FIG. 14 is a cross-sectional view of a portion of a powered surgical instrument including a handle portion according to an embodiment of the present disclosure.

A cut-away view of drive motor casing 212, surrounding drive motor 210, is illustrated in FIGS. 4-7, 9-10 and 14. Drive motor casing 212 includes a plurality of slots 214 (three slots 214a, 214b and 214c are illustrated) therein. Each slot 214 is matable with a position lock 216 to maintain drive gear 210 in a desired position. For example, in FIG. 5, position lock 216 is shown mated with slot 214a—corresponding to drive gear 200 being in its first position. In FIG. 7, position lock 216 is shown mated with slot 214b—corresponding to drive gear 200 being in its second position. FIGS. 9, 10 and 14 illustrate position lock 216 mated with slot 214c—corresponding to drive gear 200 being in its third position. Position lock 216, in the illustrated embodiments, is spring-loaded towards drive motor casing 212, which helps place and maintain drive motor 210 is a desired position.

In the illustrated embodiments, shift motor 220 is located proximally of drive motor 210 and is configured to translate drive motor 210 along drive gear axis C-C between its first, second and third positions. Referring to FIG. 10, shift motor 220 is illustrated as driving a shift screw 222 in conjunction with an internally-threaded screw housing 223 (see FIG. 10), in accordance with a disclosed embodiment. It is further disclosed that a shift sensor 224 (see FIG. 4) (e.g., micro switch or optical/ferromagnetic proximity sensor activated by position lock 216), disposed adjacent position lock 216, electrically communicates with at least one switch 124 to start or stop shift motor 220 and/or provides feedback relating to the position of drive motor 210, for example the mode of operation for powered surgical instrument 100 is desirably displayed on screen 122. For instance, the position of drive motor 210 may be indicated on screen 122 of user interface 120.

With reference to FIGS. 5 and 6, the first position of drive gear 200 is illustrated. Here, a ring gear 230 or rotation member is disposed within housing 110 and rotation of ring gear 230 causes rotation of endoscopic portion 140, end effector 160 and a distal housing portion 110a of powered surgical instrument 100. It is envisioned that an inner surface of ring 230 includes threads and/or teeth to engage drive gear 200, and is attached to distal housing portion 110a, which is disposed distally of a proximal housing portion 110b. Further, distal housing portion 110a is rotatable with respect to proximal housing portion 110b via a peripherally disposed channel 232 disposed within distal housing portion 110a and a corresponding peripherally disposed flange 234 disposed within proximal housing portion 110b.

In an embodiment, ring gear 230 is rigidly secured within distal housing portion 110a and is matingly engagable with drive gear 200. Thus, rotation of drive gear 200 causes ring gear 230, and thus distal housing portion 110a to rotate. In FIG. 2, a lip 235 is shown which isolates a user's hand from rotatable distal housing portion 110a. It is envisioned that a plurality of washers or ball-bearings (possibly made from synthetic resinous fluorine-containing polymers sold under the trademark Teflon®) are disposed between distal housing portion 110a and proximal housing portion 110b to reduce the rotational friction therebetween.

With continued reference to the embodiment illustrated in FIG. 6, a plurality of detents 231 is disposed around a surface 233 of distal housing portion 110a. A tab 237 is shown disposed on proximal housing portion 110b and may comprise a pawl or spring-biased member. In a disclosed embodiment, tab 237 is distally biased and in mechanical cooperation with at least one of plurality of detents 231. The combination of detents 231 and tab 237 helps secure distal housing portion 110a in a rotational position with respect to proximal housing portion 110b. Further, detents 231 and tab 237 may be provided to give the user audible and/or tactile feedback when endoscopic portion 140 is rotated. In a disclosed embodiment, a three-position solenoid may be used to lock the rotational position of end effector 160 once the desired rotational position is selected.

In FIG. 7, drive gear 200 is illustrated in its second position, as position lock 216 is aligned with slot 214b. Here, drive gear 200 is matingly engaged with an articulation gear 240, which is disposed at least partially within housing 110. Rotation of articulation gear 240 causes end effector 160 to move from its first position, where longitudinal axis B-B is substantially aligned with longitudinal axis A-A, towards a position in which longitudinal axis B-B is disposed at an angle to longitudinal axis A-A. Preferably, a plurality of articulated positions are achieved.

In the illustrated embodiments and with specific reference to FIGS. 7 and 8, articulation of end effector 160 is affected by an articulation gear 240, an articulation screw 242, an articulation linkage 244 and at least one articulation rod 260. More specifically, articulation gear 240 is rigidly mounted to articulation screw 242, such that as articulation gear 240 is rotated by rotation of drive gear 200 while in its second position, articulation screw 242 also rotates. A plurality of bearings 262 is illustrated at various locations on articulation screw 242 to facilitate the retaining and aligning of articulation screw drive 242 as well as reducing the friction between articulation screw 242 and housing 110, for example.

With continued reference to FIG. 7, articulation screw 242 includes a threaded portion 246, which extends through an internally-threaded portion 248 of articulation linkage 244. This relationship between articulation screw 242 and articulation linkage 244 causes articulation linkage 244 to move distally and/or proximally (in the directions of arrows D and E) along threaded portion 246 of articulation screw 242 upon rotation of articulation screw 242. For example, as articulation screw 242 rotates in a first direction (e.g., clockwise), articulation linkage 244 move proximally, and as articulation screw 242 rotates in a second direction (e.g., counter-clockwise), articulation linkage 244 move distally.

At least one articulation arm 250 is shown extending from articulation linkage 244. In an embodiment, articulation arm 250 is rigidly connected to articulation rod 260 and it is envisioned that more than one articulation arm 250 is connectable to more than one articulation rod 260. As articulation linkage 244 is translated distally and/or proximally in response to rotation of articulation gear 240, articulation rod(s) 260 is also translated distally and/or proximally (in the directions of arrows F and G, along longitudinal axis A-A) in response thereto. Any combinations of limits switches, proximity sensors (e.g., optical and/or ferromagnetic), linear variable displacement transducers and shaft encoders (disposed within housing 110, for instance) may be utilized to control and/or record the location of articulation linkage 244 and/or articulation angle of end effector 160 and/or position of a firing rod 306 (as discussed below with reference to FIGS. 9 and 11).

Figure 8A:
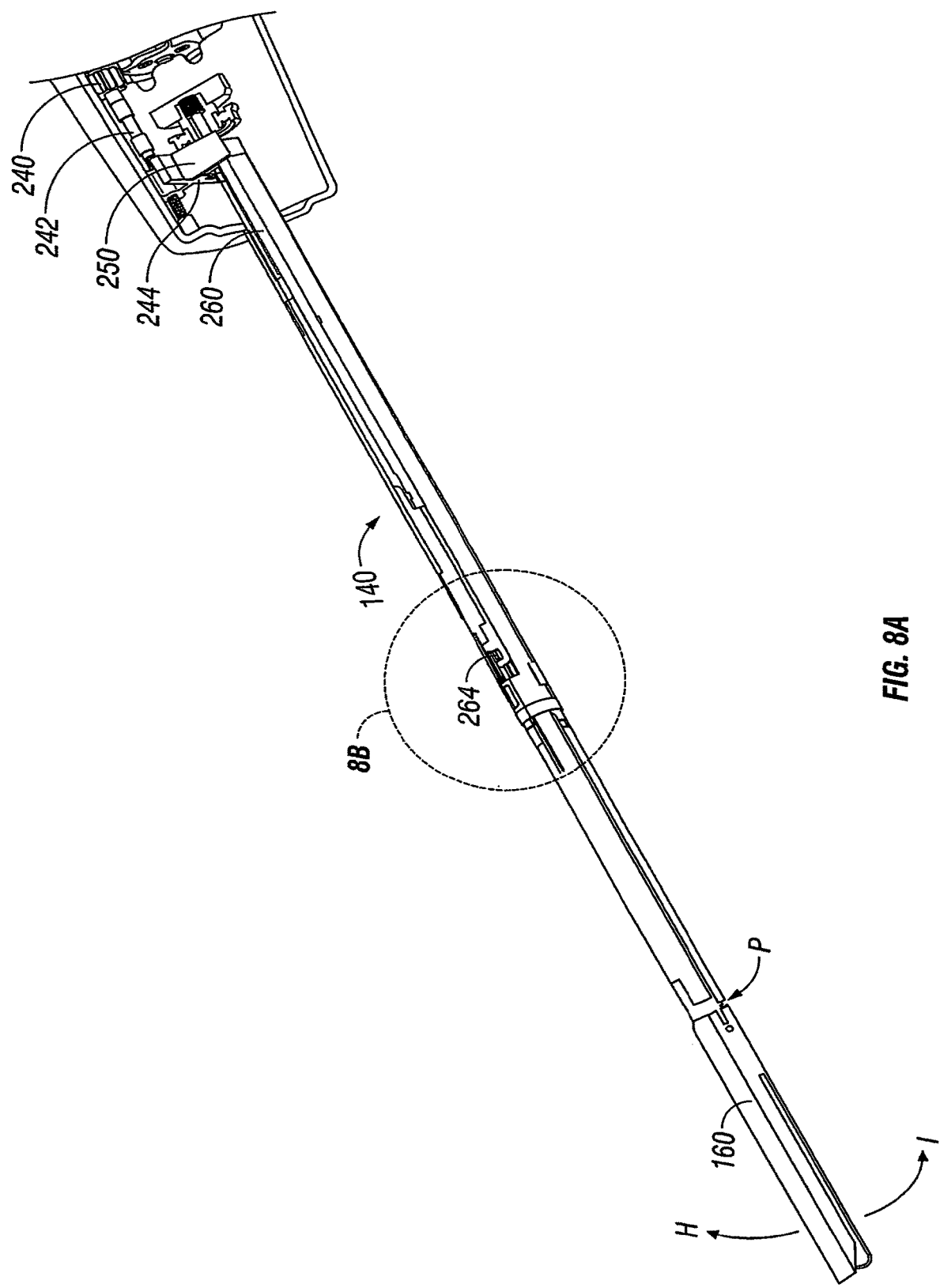
FIG. 8A is a partial perspective view including an endoscopic portion of the powered surgical instrument of FIGS. 1-7 according to an embodiment of the present disclosure.
Figure 8B:
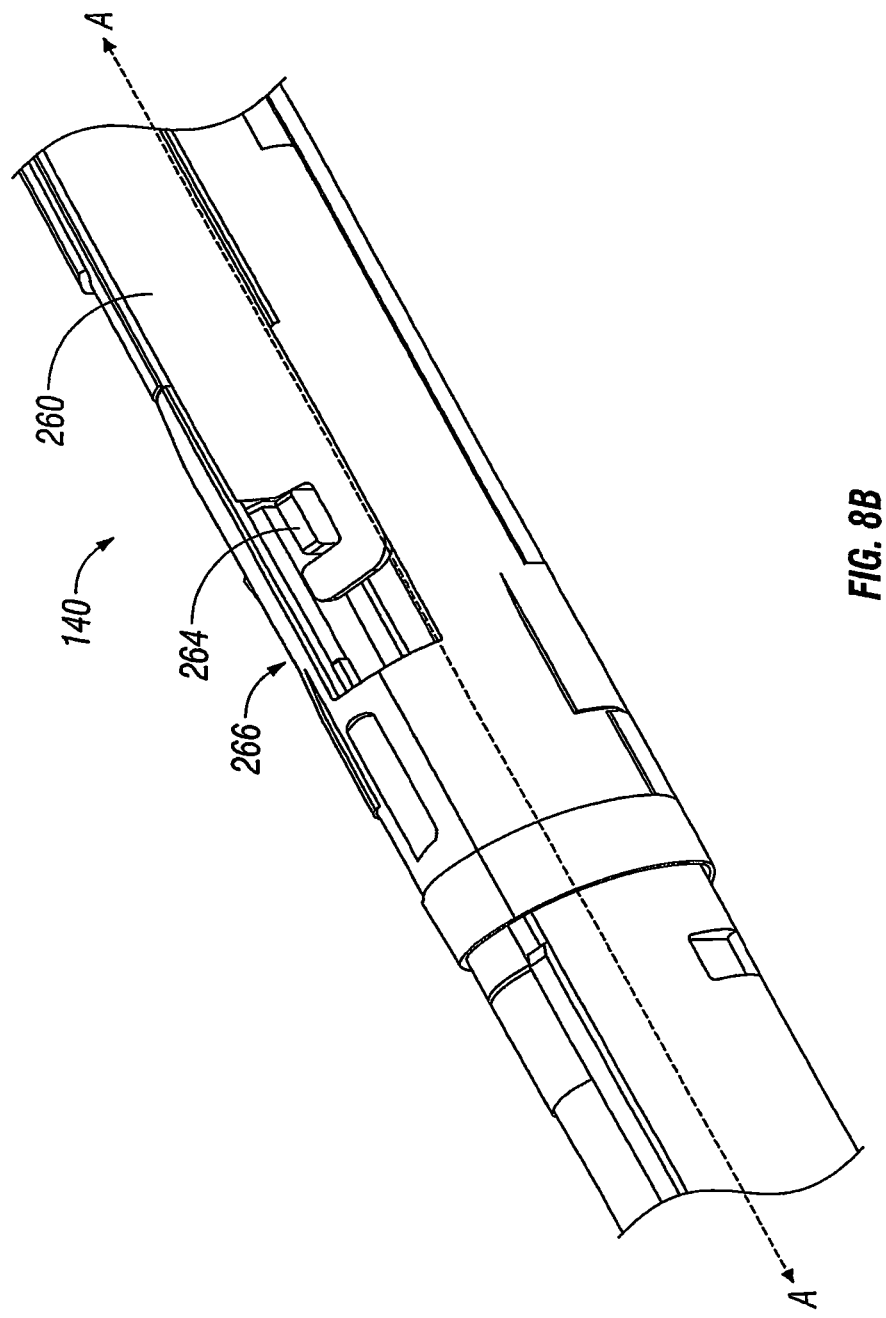
FIG. 8B is an enlarged perspective view of a portion of the powered surgical instrument indicated in FIG. 8A.

With reference to FIGS. 8A and 8B, articulation rod 260 is shown extending through at least a portion of endoscopic portion 140 and in mechanical cooperation with a linkage rod 264. Thus, linkage rod 264 similarly moves along longitudinal axis A-A upon rotation of articulation gear 240. A distal portion 266 of linkage rod 264 is in mechanical cooperation with end effector 160, such that proximal and distal movement of linkage rod 264 causes end effector 160 to move from its first position towards its second position about pivot P. For example, linkage rod 264 is connected to end effector 160 at a location offset laterally from pivot P. More specifically, and for illustrative purposes, as linkage rod 264 moves distally, end effector 160 is articulated in the direction of arrow H and as linkage rod 264 is translated proximally, end effector 160 is articulated in the direction of arrow I. It is also envisioned that a portion of articulation rod 260 is in mechanical cooperation with end effector 160 to affect articulation thereof. Further details of providing articulation to end effector 160 are described in detail in commonly-owned U.S. Pat. No. 6,953,139 to Milliman et al., the contents of which are hereby incorporated by reference in their entirety.

According to an embodiment of the present disclosure, end effector 160 includes a cartridge assembly (e.g., jaw member 164) and an anvil assembly (e.g., jaw member 162) including an anvil portion for deploying surgical fasteners into body tissue and forming the surgical fasteners. End effector 160 is pivotably mounted about an axis substantially perpendicular to the longitudinal axis of endoscopic portion 140. Cartridge assembly 164 houses a plurality of staples. Anvil assembly 162 is movable in relation to cartridge assembly 164 between an open position spaced from cartridge assembly 164 and an approximated or clamped position in juxtaposed alignment with cartridge assembly 164. Preferably, the staples are housed in cartridge assembly 164 to apply linear rows of staples to body tissue. End effector 160 is attached to a mounting portion, which is pivotably attached to a body portion. The body portion may be integral with endoscopic portion 140 of powered surgical instrument 100, or may be removably attached thereto to provide a replaceable or disposable loading unit. The loading unit may be connectable to endoscopic portion 140 through a bayonet connection. It is envisioned that the loading unit has an articulation link connected to the mounting portion of the loading unit and the articulation link is connected to the linkage rod so that the end effector 160 is articulated as the linkage rod is translated in the distal-proximal direction along the longitudinal axis. Other means of connecting end effector 160 to endoscopic portion 140 to allow articulation may be used. For example, a flexible tube or a plurality of pivotable members may be used.

Figure 15A:
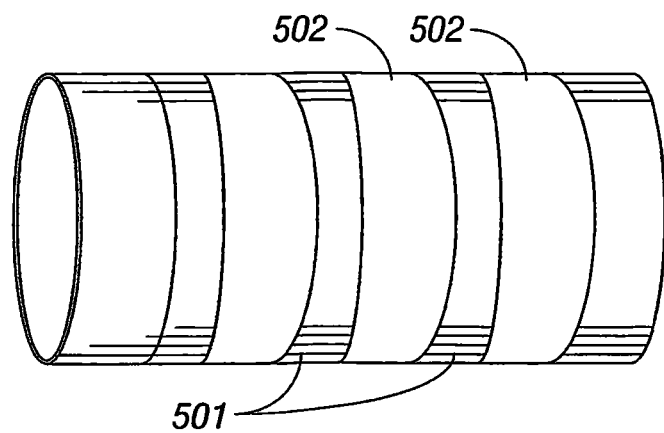
FIGS. 15A-B are perspective views of an articulating shaft of the distal portion of the powered surgical instrument of FIG. 1 according to an embodiment of the present disclosure.
Figure 15B:
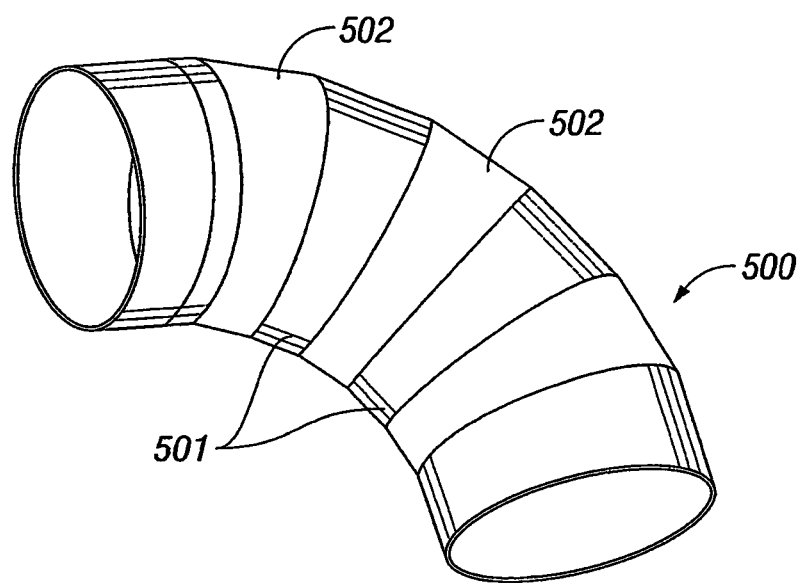

A loading unit may incorporate (or be configured to incorporate) various end effectors, such as vessel sealing devices, linear stapling devices, circular stapling devices, cutters, etc. Such end effectors may be coupled to endoscopic portion 140 of powered surgical instrument 100. An intermediate flexible shaft 500 may be included between handle portion 112 and loading unit. For example, as shown in FIGS. 15A-B, endoscopic and distal portions 140, 142 are shown as a flexible shaft 500. Flexible shaft 500 includes a plurality of interconnected angled outer tubes 501 and 502. FIG. 15A shows flexible shaft in a non-articulated formation and FIG. 15B shows flexible shaft 500 in an articulated formation. When flexible shaft 500 is straight, narrow sections of tubes 501 alternate with the wide sections of tubes 502 as shown in FIG. 15A. When flexible shaft 500 is fully articulated, the short sides and the wide sides of tubes 501 and 502 are aligned, as shown in FIG. 15B. Such a flexible shaft 500 may facilitate access in certain areas of the body.

Further, where various loading units can be used, a digital control module (DCM) 130 (FIG. 4) can control the force being applied to rod 306 so that rod 306 can drive the particular end effector that is on the loading unit in use at the time. For clarity, wires are not shown in the Figures connecting DCM 130 to various components of powered surgical instrument 100, but such wires are contemplated by the present disclosure. The loading unit may also include a mechanical or electronic sensor that indicates to DCM 130 which end effector is on the loading unit. In an embodiment, DCM 130 is also capable of storing information relating to the force applied to rod 306. Additionally, the voltage and current from drive motor 210 may be measured to provide information and/or feedback regarding the state of powered surgical instrument 100. For instance, if the user is attempting to clamp down on tissue that is too thick, the voltage and/or current will increase. This information can be provided to the user and/or the power can be interrupted or ceased. It is envisioned that such a feature helps prevent damage to the mechanisms in the instrument.

With reference to FIGS. 9-11 and 14, drive gear 200 is illustrated in its third position, with position lock 216 aligned with slot 214c. Here, drive gear 200 is matingly engaged with an actuator gear 300, which is disposed at least partially within housing 110. More specifically, a set of teeth 202 disposed on a face 204 (FIG. 4) of drive gear 200 matingly engage teeth on actuator gear 300 to provide at least one of grasping tissue, clamping tissue, and firing of end effector 160 (e.g., stapling and cutting) and retracting elements to their original position.

Figure 11:
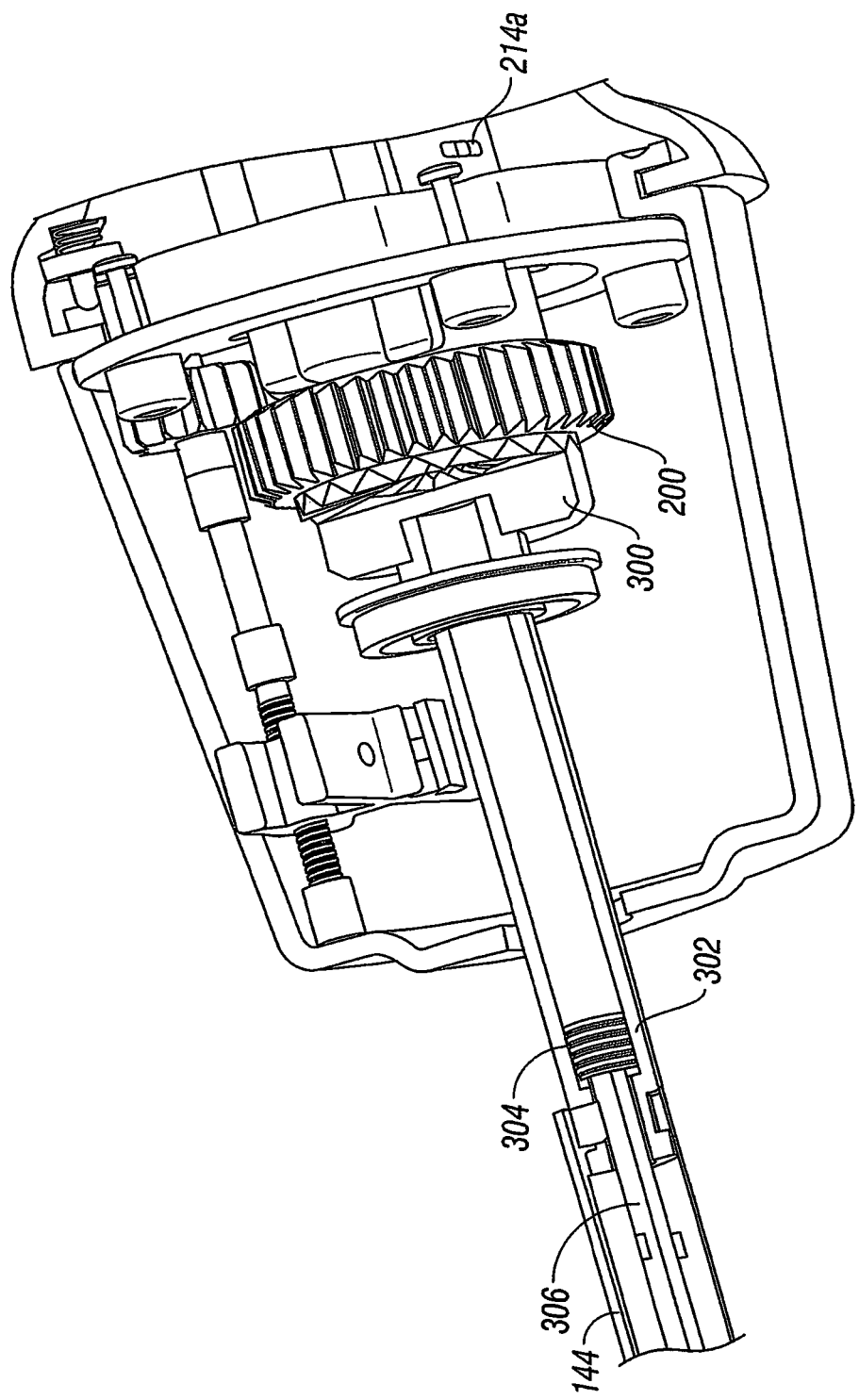

With continued reference to FIGS. 9 and 11, a drive tube 302, a bung 304 and firing rod 306 are also included. Drive tube 302 includes internal threads (not explicitly shown) along at least a portion of its length and is rigidly attached to actuator gear 300. Bung 304 is threadably engaged with internal threads of drive tube 302 and is translatable within drive tube 302 with respect to actuator gear 300. FIG. 9 shows bung 304 near its proximal-most position and FIG. 11 illustrates bung 304 near its distal-most position. Firing rod 306 is rigidly connected to bung 304 and extends distally therefrom. In an embodiment of the disclosure, firing rod 306 extends at least to distal portion 142 of endoscopic portion 140.

In response to rotation of drive gear 200, actuator gear 300 and drive tube 302 also rotate. As drive tube 302 rotates, bung 304 and firing rod 306 are translated proximally and/or distally within the confines of drive tube 302. Distal translation of firing rod 306 (corresponding with a clockwise rotation of drive gear 200, for instance) can cause jaw members 162, 164 (see FIG. 1) of end effector 160 to grasp or clamp tissue held therebetween. Additional distal translation of firing rod 306 may cause surgical fasteners to be ejected from end effector 160 (e.g., via cam bars and/or an actuation sled (neither of which are explicitly shown in this embodiment)) to fasten tissue and may also cause a knife (not explicitly shown in this embodiment) to sever tissue. Proximal translation of firing rod 306 (corresponding with a counter-clockwise rotation of drive gear 200, for instance) can cause jaw members 162, 164 and/or knife to return to their pre-fired positions. Further details of firing and otherwise actuating end effector 160 are described in detail in commonly-owned U.S. Pat. No. 6,953,139 to Milliman et al., the entire contents of which are hereby incorporated by reference herein.

In an embodiment of the disclosure, the anvil portion of end effector 160 includes a cam surface for being engaged by the drive assembly of end effector 160. The drive assembly includes a drive beam, which desirably has a knife for cutting tissue. The drive beam has a cam roller positioned to engage the cam surface, and a flange positioned to engage the cartridge assembly to effect approximation of the anvil assembly 162 and cartridge assembly 164 with respect to one another when the drive beam is advanced distally. In addition, when advanced further in the distal direction, the drive beam engages an actuation member for deploying the surgical fasteners from the cartridge assembly, as disclosed in the Milliman 139 patent.

Any combination of sensors may be positioned within powered surgical instrument 100 to determine the position of various components and/or its operating stage, e.g., articulation, rotation, clamping, firing of end effector 160. For example, limit switches, proximity sensors (e.g., linear and/or ferromagnetic), potentiometers, linear variable displacement transducers (LVDT), shaft encoders, etc., may be used to help control and/or record the location of articulation linkage 244, firing rod 306 and/or ring gear 230, as discussed above.

Figure 12:
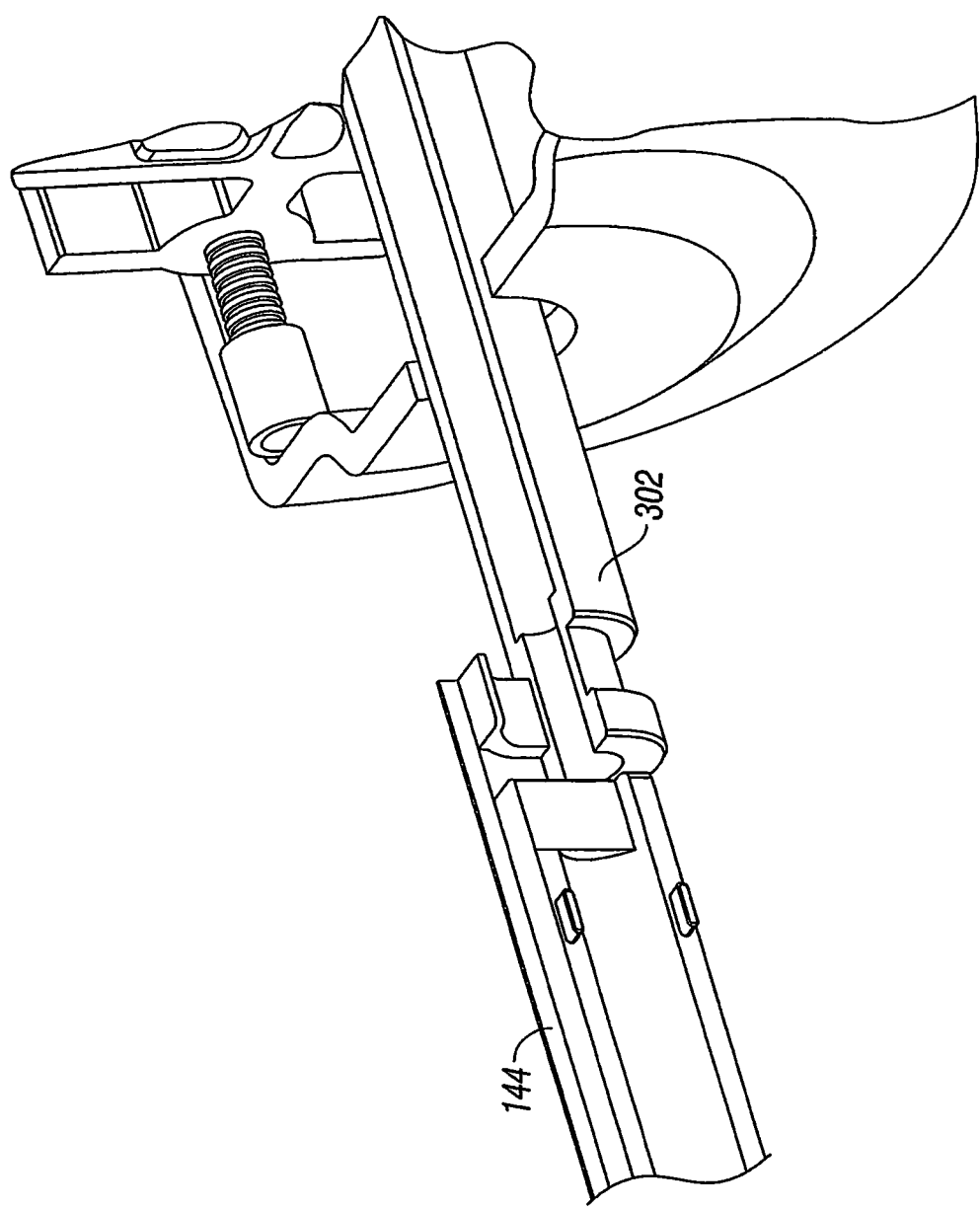
FIGS. 12 and 13 are enlarged perspective views of portions of the powered surgical instrument of FIGS. 1-11 according to an embodiment of the present disclosure.
Figure 13:
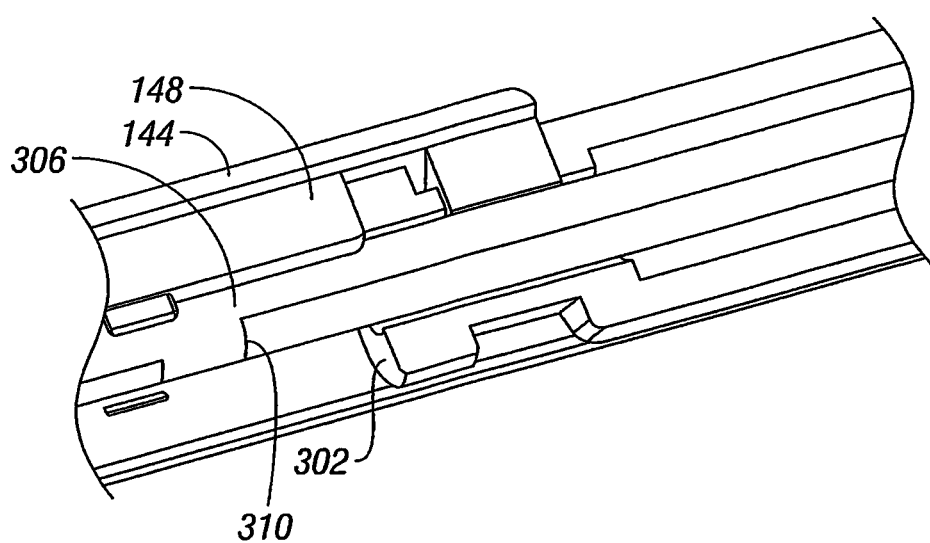

Referring now to FIGS. 9, 11 and 12, endoscopic portion 140 includes a tube housing 144 that extends from an area adjacent housing 110 towards end effector 160. As drive tube 302 rotates, end effector 160 does not rotate as a direct consequence thereof. Referring to FIG. 13, tube housing 144 includes flat portions 148 thereon, which correspond to flat portions 310 of firing rod 306. The pair of flat portions 148 and 310 helps prevent rotation of firing rod 306 by helping to limit firing rod 306 to axial movement.

With reference to FIG. 9, a drive motor shaft 218 is shown extending from drive motor 210 and being connected to drive gear 200. A fastener (not explicitly shown in this embodiment) may be used to retain drive gear 220 on drive motor shaft 218. Drive motor shaft 218 is rotated by drive motor 210, thus resulting in rotation of drive gear 220. Drive motor shaft 218 is shown having a flat portion 219 (more than one flat portions 219 may be included), which allows "play" or "rotational float" between drive gear 220 and drive motor shaft 218 to facilitate tooth alignment of the gears and to help enable drive gear 220 to shift between positions. FIG. 9 also illustrates a bearing 308 disposed within housing 110 and at least partially surrounding drive tube 302. Bearing 308 facilitates rotation of drive tube 302 and helps to align drive tube 302 through endoscopic portion 140 and supports all thrust loading between drive gear 200 and actuator gear 300.

In FIG. 10, a transducer 420 is shown adjacent drive motor 210 and shift motor 220. Transducer 420 (e.g., a force or pressure transducer) may measure and/or control the force required for the desired pressure on actuator gear 300. Transducer 420 may be in communication with portions of user interface 120, which may provide feedback to a user. Additionally, spring coupling 430 is illustrated between drive motor 210 and shift motor 220. Specifically, in a disclosed embodiment, spring coupling 430 includes a spring 432 mounted in a telescoping cage 434. Shift screw 222 is shown extending through spring 432 and may be configured to apply a compressive load on spring 432. It is envisioned that cage 434 is collapsible as spring 432 is compressed. The force applied to drive motor 210 may be adjusted using spring 432 and/or cage 434.

In an embodiment of the disclosure, drive gear 200 and actuator gear 300 form a clutch face. The gear teeth are arranged to slip unless a threshold force is applied to drive motor 210 by shift motor 200 and a spring coupling 430 (as discussed below in connection with FIG. 10) disposed therebetween. Further, when shift motor 200 and spring coupling 430 apply the threshold force needed for drive gear 200 and actuator gear 300 to engage without slipping, rod 306 will be driven distally. Telescoping cage 434 may include a stop incorporated therewith, such that cage 434 will retract rod 306, rather than decompress spring coupling 430.

With reference to FIG. 3, user interface 120 is shown including screen 122 and seven switches 124a-124g. In the illustrated embodiment, user interface displays the "mode" (e.g., rotation, articulation or actuation), which may be communicated to user interface 120 via shift sensor 224 (FIG. 4), "status" (e.g., angle of articulation, speed of rotation, or type of actuation) and "feedback," such as whether staples have been fired. Switch 124a is shown having an "M," standing for mode, which may be used to position drive gear 200 via shift motor 220 for selecting between rotation, articulation, grasping, clamping and firing. It is also envisioned that switch 124a can be used to let a user input different tissue types, and various sizes and lengths of staple cartridges.

Switches 124b-124e on user interface 120 are shown with arrows thereon and may be used for selecting the direction, speed and/or torque at which drive gear 200 is rotated by drive motor 210. It is also envisioned that at least one switch 124 can be used for selecting an emergency mode that overrides various settings, for example. Further, switches 124f and 124g are illustrated having an "N" and a "Y" thereon. It is envisioned that switches 124f and 124g may be used for helping a user navigate and select various setting of powered surgical instrument 100. The indicia on switches 124a-124g and their respective functions are not limited by what is shown in the accompanying figures, as deviations therefrom are contemplated and within the scope of the present disclosure. Additionally, and with reference to FIGS. 1 and 2, buttons 114a and 114b may be used for starting and/or stopping movement of drive motor 210 and/or shift motor 220. Other functions for buttons 114 and 114b are also anticipated as well as having more or fewer buttons 114. In a particular embodiment, switches 124a-124g may include one or more microelectronic membrane switches, for example. Such a microelectronic membrane switch includes a relatively low actuation force, small package size, ergonomic size and shape, low profile, the ability to include molded letters on the switch, symbols, depictions and/or indications, and a low material cost. Further, switches 124a-124g (such as microelectronic membrane switches) may be sealed to help facilitate sterilization of powered surgical instrument 100, as well as helping to prevent particle and/or fluid contamination.

As an alternative to, or in addition to switches 124 or buttons 114, other input devices may include voice input technology, which may include hardware and/or software incorporated in a digital control module (DCM) 130 (FIG. 4), or a separate digital module connected to DCM 130. The voice input technology may include voice recognition, voice activation, voice rectification and/or embedded speech. The user may be able to control the operation of the instrument in whole or in part through voice commands, thus freeing one or both of the user's hands for operating other instruments. Voice or other audible output may also be used to provide the user with feedback.

In an embodiment, spring coupling 430 is used in the feedback and control of powered surgical instrument 100. As described above, DCM 130 may be connected to one or more buttons 114 or switches 124 and one or more display screens 122 to provide feedback to the user and for helping to control the operation of powered surgical instrument 100. DCM 130 may be a digital board incorporated in housing 110 of powered surgical instrument 100. Spring coupling 430 may include a pressure transducer that can interact with DCM 130 to control the force being applied to rod 306.

It is also envisioned that user interface 120 includes different colors and/or intensities of text on screen 122 and/or on switches 124a-124g for further differentiation between the displayed items. User feedback can also be included in the form of pulsed patterns of light, acoustic feedback (e.g., buzzers, bells or beeps that may be sounded at selected time intervals), verbal feedback, and/or haptic vibratory feedback (such as an asynchronous motor or solenoids), for example. The visual, auditory or haptic feedback can be increased or decreased in intensity. For example, the intensity of the feedback may be used to indicate that the forces on the instrument are becoming excessive. Additionally, switches 124a-124g may be positioned at different heights from one another and/or may include raised indicia or other textural features (e.g., concavity or convexity) to allow a user to depress an appropriate switch 124 without the need to look at user interface 120. Further, proximal housing portion 110b may be used as a joy stick type control system.

Additionally, user interface 120 may include a separate display screen or screens 122 and input devices (such as switches 124 or buttons 114), or the input devices may be incorporated in whole or in part in screen 122. For example, a touch screen liquid crystal display (LCD) may be used to allow the user to provide input while viewing operational feedback. The touch screen LCD may include resistive, capacitive or surface acoustic wave controls. This approach may enable facilitation of sealing screen 122 components to help sterilize powered surgical instrument 100, as well as preventing particle and/or fluid contamination. In certain embodiments, screen 122 is pivotably or rotatably mounted to powered surgical instrument 100 for flexibility in viewing screen 122 during use or preparation. Screen 122 may be hinged or ball- and socket mounted to powered surgical instrument 100, for example.

In a disclosed embodiment, at least some of the information monitored by the various sensors in powered surgical instrument 100 may be provided to a video screen or monitoring system in an operating room. For instance, the data may be transmitted to a receiver for the operating room monitoring system from a communication transmitter incorporated in or associated with powered surgical instrument 100, via technology including Blue Tooth, ANT3, KNX, Z Wave, XI0, wireless USB, WiFi, IrDa, Nanonet, Tiny OS, ZigBee, radio, UHF and VHF. Such features may facilitate monitoring by the user of powered surgical instrument 100 or other operating room or hospital personnel or remotely located persons.

Figure 4:
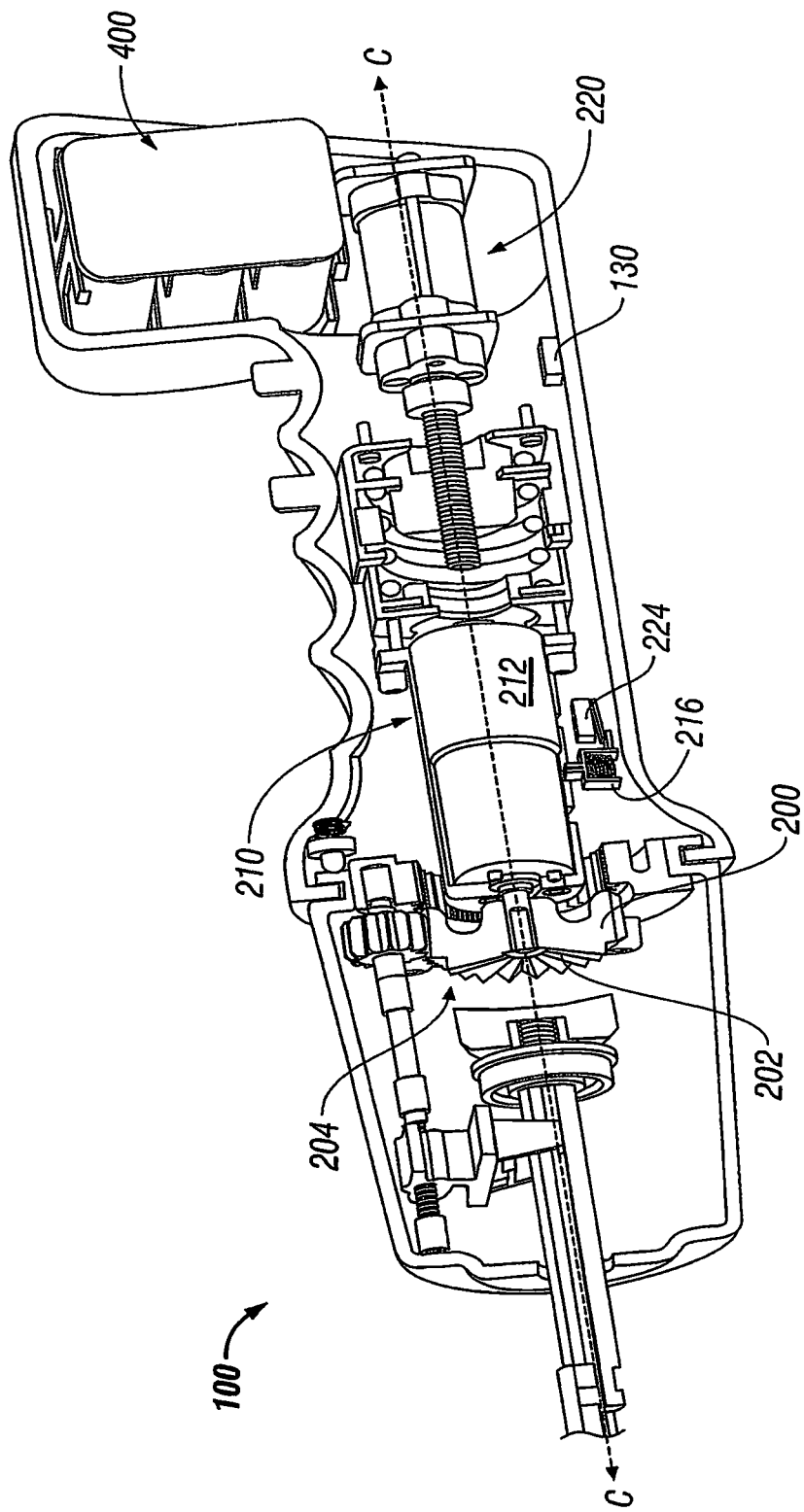
FIG. 4 is a partial perspective sectional view of internal components of the powered surgical instrument of FIGS. 1-3 in accordance with an embodiment of the present disclosure.

Referring to FIG. 4, any combination of a battery pack 400, fuel cell and/or high-energy capacitor may be used to provide power to powered surgical instrument 100. For example, capacitors may be used in conjunction with battery pack 400. Here, capacitors can be used for a burst of power when energy is desired/required more quickly than can be provided with a battery on its own (e.g., when clamping thick tissue, rapid firing, clamping, etc.), as batteries are typically slow-drain devices from which current cannot be quickly drawn. It is envisioned that batteries can be connected to capacitors to charge the capacitors.

It is also envisioned that battery pack 400 includes at least one disposable battery. The disposable battery may be between about 9 volts and about 30 volts and may be useful in a disposable surgical instrument. Other power-supplying means are also contemplated including electric power. In alternative embodiments a cord is provided to connect instrument 100 to a generator.

In a disclosed embodiment, the DCM is connected to shift motor 220 and drive motor 210 and is configured and arranged to monitor the battery 400 impedance, voltage, temperature and/or current draw and to control the operation of powered surgical instrument 100. The load or loads on battery 400, transmission, motors 220,210 and drive components of powered surgical instrument 100 are determined to control a motor speed if the load or loads indicate a damaging limitation is reached or approached. For example, the energy remaining in battery 400, the number of firings remaining, whether battery 400 must be replaced or charged, and/or approaching the potential loading limits of powered surgical instrument 100 may be determined.

The DCM can be configured and arranged to control or help control the operation of shift motor 220 and/or drive motor 210 to respond to the monitored information. Pulse modulation, which may include an electronic clutch, may be used in controlling the output. For example, the DCM can regulate the voltage or pulse modulate the voltage to adjust the power and/or torque output to prevent system damage or optimize energy usage. An electric braking circuit may be used for controlling drive motor 210 and/or shift motor 220, which uses the existing back electromotive force (EMF) of rotating drive motor 210 to counteract and substantially reduce the momentum of drive gear 200. The electric braking circuit may improve the control of drive motor 210 and/or shift motor 220 for stopping accuracy and/or shift location of powered surgical instrument 100. Sensors for monitoring components of powered surgical instrument 100 and to help prevent overloading of powered surgical instrument 100 may include thermal-type sensors, such as thermal sensors, thermistors, thermopiles, thermocouples and/or thermal infrared imaging and provide feedback to the DCM. The DCM may control the components of powered surgical instrument 100 in the event that limits are reached or approached and such control can include cutting off the power from the battery pack 400, temporarily interrupting the power or going into a pause mode, pulse modulation to limit the energy used, and the DCM can monitor the temperature of components to determine when operation can be resumed. The above uses of the DCM may be used independently of or factored with current, voltage, temperature and/or impedance measurements.

In the embodiment illustrated in FIG. 5, shift motor 220 is shown including a two-part housing 226. Each part 226a and 226b of two-part housing 226 are slidably engaged with each other. It is envisioned that part 226a is rigidly secured to drive motor casing 212, while part 226b is affixed to shift motor 220 and is translatable within housing 110. Additionally, a wiring slot 228 may be included to allow for wires (not explicitly shown in this embodiment) to pass from transducer 420 towards user interface 120, for example (see also FIG. 10).

Referring to FIG. 14, powered surgical instrument 100 is illustrated having a pistol-grip handle portion 112. Here, handle portion 112 is disposed at an angle (e.g., substantially 90°) from longitudinal axis A-A. In this embodiment, it is envisioned that at least one button 114 is disposed thereon. Additionally, user interface 120 may be positioned approximately in the position shown in FIG. 14. Further, a movable handle (not explicitly shown in this embodiment) may be employed to control various functions of powered surgical instrument 100.

It is envisioned that end effector 160 is reusable, can accept a staple cartridge and/or is part of a disposable loading unit. Further details of a disposable loading unit are described in detail in commonly-owned U.S. Pat. No. 5,752,644 to Bolanos et al., the entire contents of which are hereby incorporated by reference herein. Disposable and/or replaceable loading units can include end effectors without articulation, as disclosed in U.S. Pat. No. 6,953,139 to Milliman et al., previously incorporated by reference. A switch may be provided adjacent handle portion 112 to deactivate the second position of shift motor 220 electronically. Other means, such as mechanical means, may also be used.

A disposable or replaceable loading unit incorporating a surgical end effector 160, in certain embodiments of the present disclosure, includes sensors positioned within the loading unit to determine the position of various components and/or operation of end effector 160, such as articulation, rotation, clamping and firing of end effector 160. For example, electrical contacts, proximity sensors, optical sensors, photo diodes, and/or mechanical or metallic sensors are used to control and/or record information concerning the end effector 160. The location of the anvil assembly 162 and cartridge assembly 164 with respect to one another, the articulated or non-articulated position of end effector 160, rotation of end effector 160, and/or correct loading of the loading unit, staple cartridge and/or components of the staple cartridge may also be determined.

An identification system may also be included to determine and communicate to the DCM various information, including the speed, power, torque, clamping, travel length and strength limitations for operating the particular end effector 160. The DCM may also determine the operational mode and adjust the voltage, clutch spring loading and stop points for travel of the components. More specifically, the identification system may include a component (e.g., a microchip, emitter or transmitter) in end effector 160 that communicates (e.g., wirelessly, via infrared signals, etc.) with the DCM, or a receiver therein. It is also envisioned that a signal may be sent via firing rod 306, such that firing rod 306 functions as a conduit for communications between the DCM and end effector 160.

The loading unit, in certain embodiments according to the present disclosure, includes an axial drive assembly that cooperates with firing rod 306 to approximate anvil assembly 162 and cartridge assembly 164 of end effector 160, and fire staples from the staple cartridge. The axial drive assembly may include a beam that travels distally through the staple cartridge and may be retracted after the staples have been fired, as disclosed in certain embodiments of U.S. Pat. No. 6,953,139 to Milliman et al., the disclosure of which is hereby incorporated by reference herein. By way of example, the sensors discussed above may be used to determine if the staples have been fired from the staple cartridge, whether they have been fully fired, whether and the extent to which the beam has been retracted proximally through the staple cartridge and other information regarding the operation of the loading unit. In certain embodiments of the present disclosure, the loading unit incorporates components for identifying the type of loading unit, and/or staple cartridge loaded on the instrument 100, including infrared, cellular, or radio frequency identification chips (such as Sensormatic or similar technology). The type of loading unit and/or staple cartridge may be received by an associated receiver within the DCM, or an external device in the operating room for providing feedback, control and/or inventory analysis. The power or battery pack 400 can incorporate a component for identifying the type of power pack 400 loaded with powered surgical instrument 100 or for sending feedback concerning the status of power pack 400.

In certain embodiments of the present disclosure, powered surgical instrument 100 includes disposable or replaceable loading units incorporating a surgical end effector 160 and a reusable portion including a housing 110 and endoscopic portion 140 that is removably attached to the loading unit. The reusable portion may be configured for sterilization and re-use in a subsequent surgical procedure. In an embodiment, the components of the housing 110 are sealed against infiltration of particulate and/or fluid contamination and help prevent damage of the component by the sterilization process. Power pack 400, in certain embodiments according to the present disclosure, comprises a rechargeable battery. The rechargeable battery can be connected to contacts accessible at housing 110 of the instrument 100, for example, or, rechargeable battery may be rechargeable through an inductive charging interface sealed within housing 110. The inductive charging interface may eliminate shorting of contacts and provides an internal battery that may be hermetically or liquid resistance sealed.

The present disclosure also relates to a method of applying surgical fasteners to tissue. The method includes the use of powered surgical instrument 100, as described above.

Now referring to FIGS. 16-19, a powered surgical instrument, e.g., a surgical stapler, in accordance with other embodiments of the present disclosure is referred to as reference numeral 1000. Powered surgical instrument 1000 includes a housing 1100, an endoscopic portion 1400 defining a first longitudinal axis D-D extending therethrough, a shaft portion 1500 and an end effector 1600 defining a second longitudinal axis E-E extending therethrough. Further details of powered surgical instrument 1000 are included in U.S. patent application Ser. No. 11/786,933, filed on Apr. 13, 2007 (now U.S. Pat. No. 8,800,837), the entire contents of which are hereby incorporated by reference herein. While the features of the embodiments illustrated in FIGS. 16-19 are shown in connection with a particular type of surgical instrument 1000, it is envisioned that the features described with respect to FIGS. 16-19 are operable with other surgical instruments, such as powered surgical instrument 100 of FIGS. 1-15.

Figure 16:
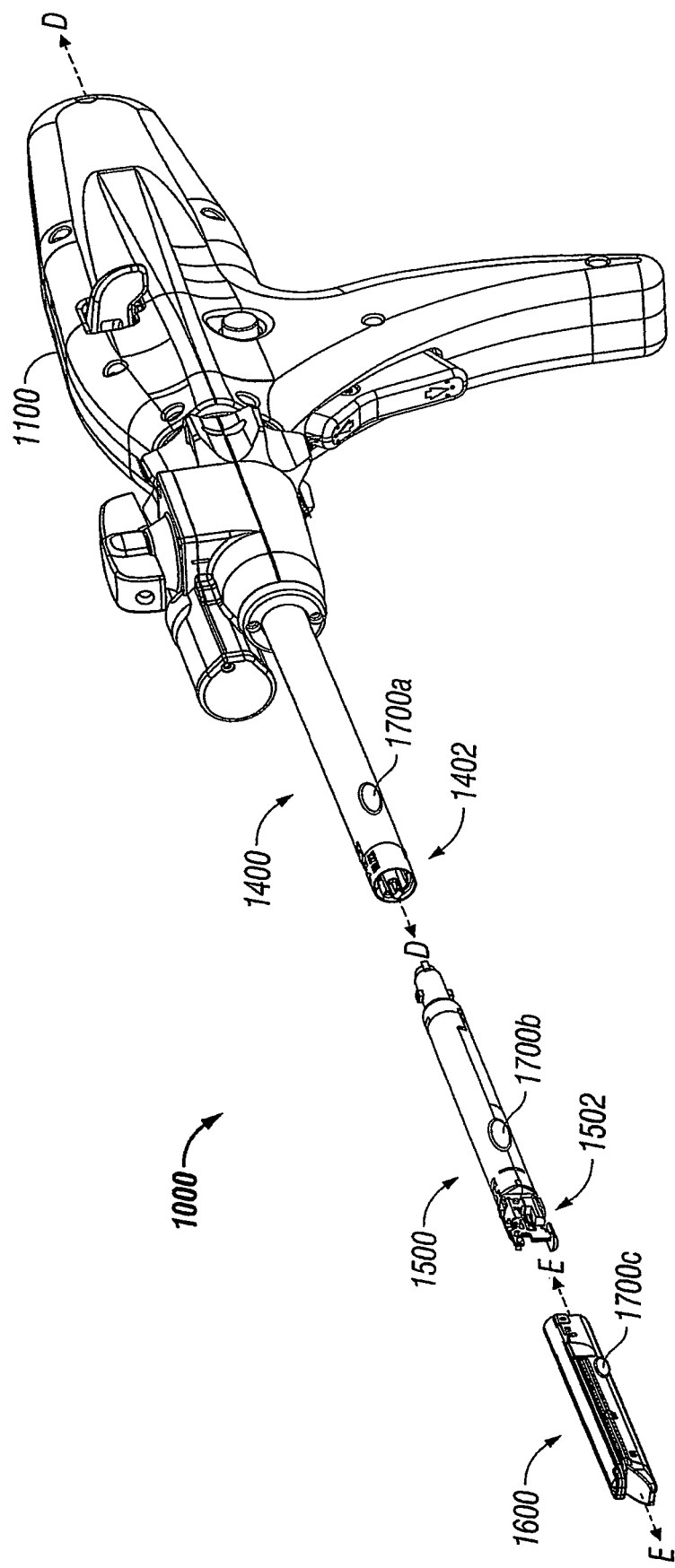
FIG. 16 is a perspective view of a powered surgical instrument having a selectively connectable shaft portion according to an embodiment of the present disclosure.
Figure 17A:
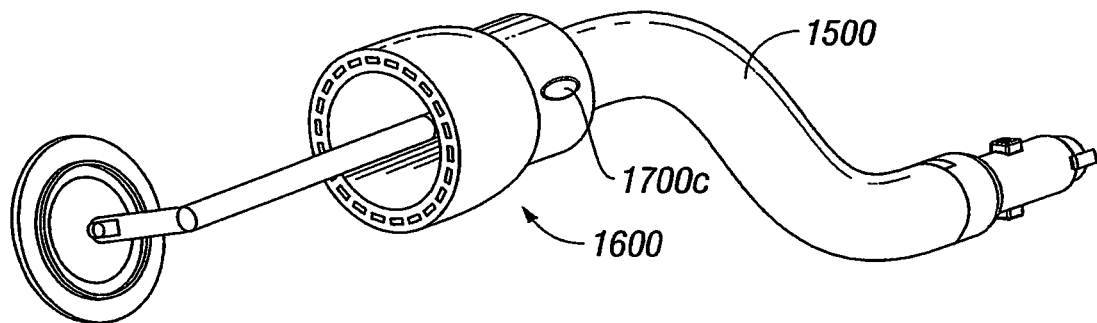
FIGS. 17A-17C are each perspective views of end effector having circular staple cartridges engaged with a shaft portion, each shaft portion being connectable with the powered surgical instrument of FIG. 16.
Figure 17B:
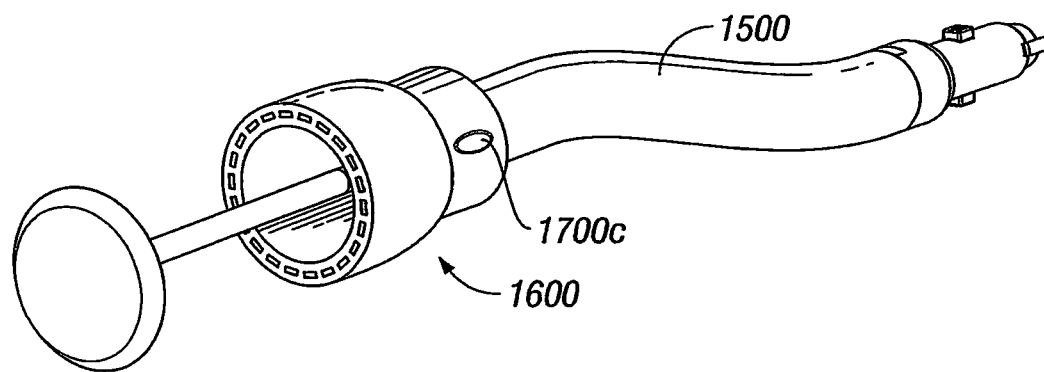
Figure 17C:
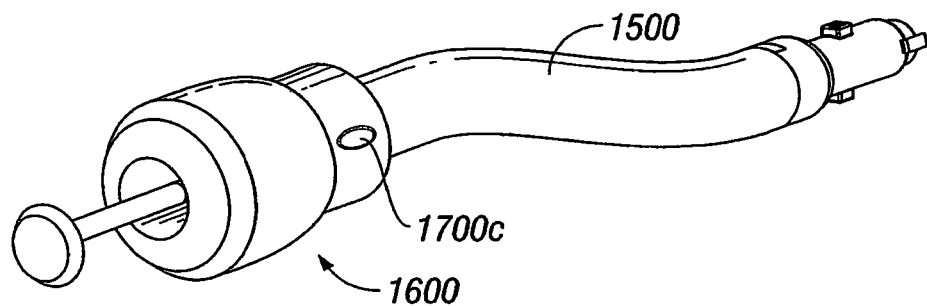
Figure 18:
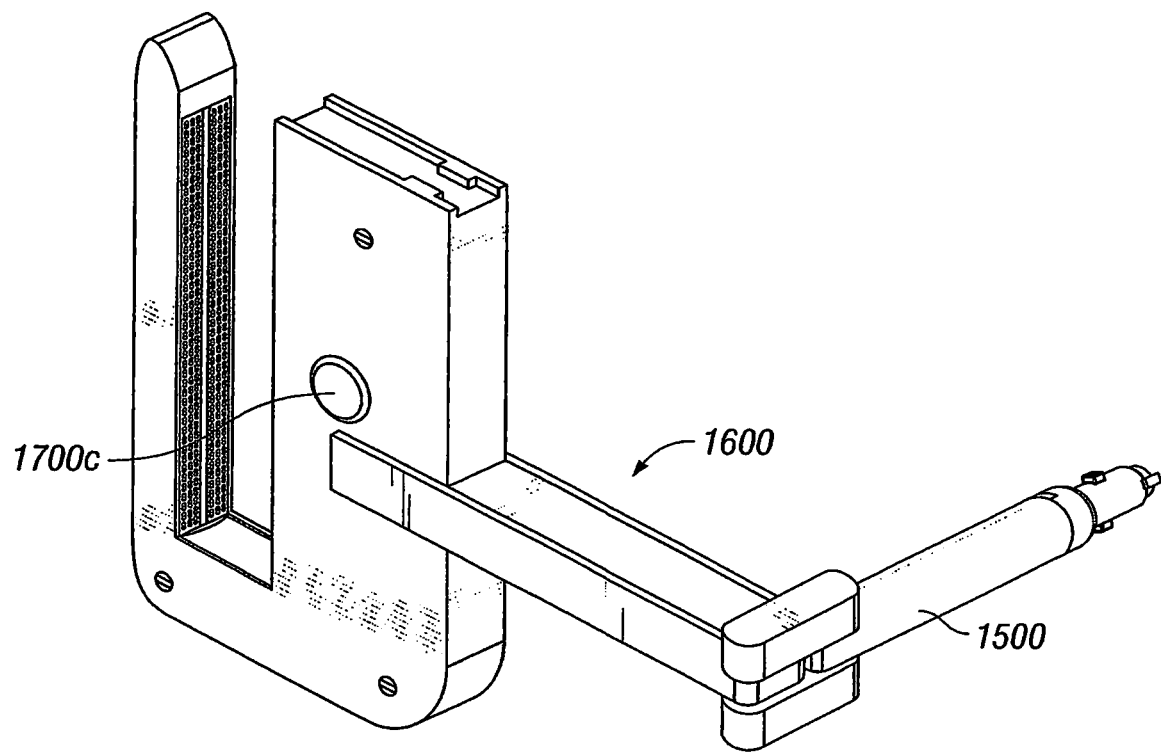
FIG. 18 is a perspective view of an end effector having parallel jaw member engaged with a shaft portion, the shaft portion being connectable with the powered surgical instrument of FIG. 16.
Figure 19:
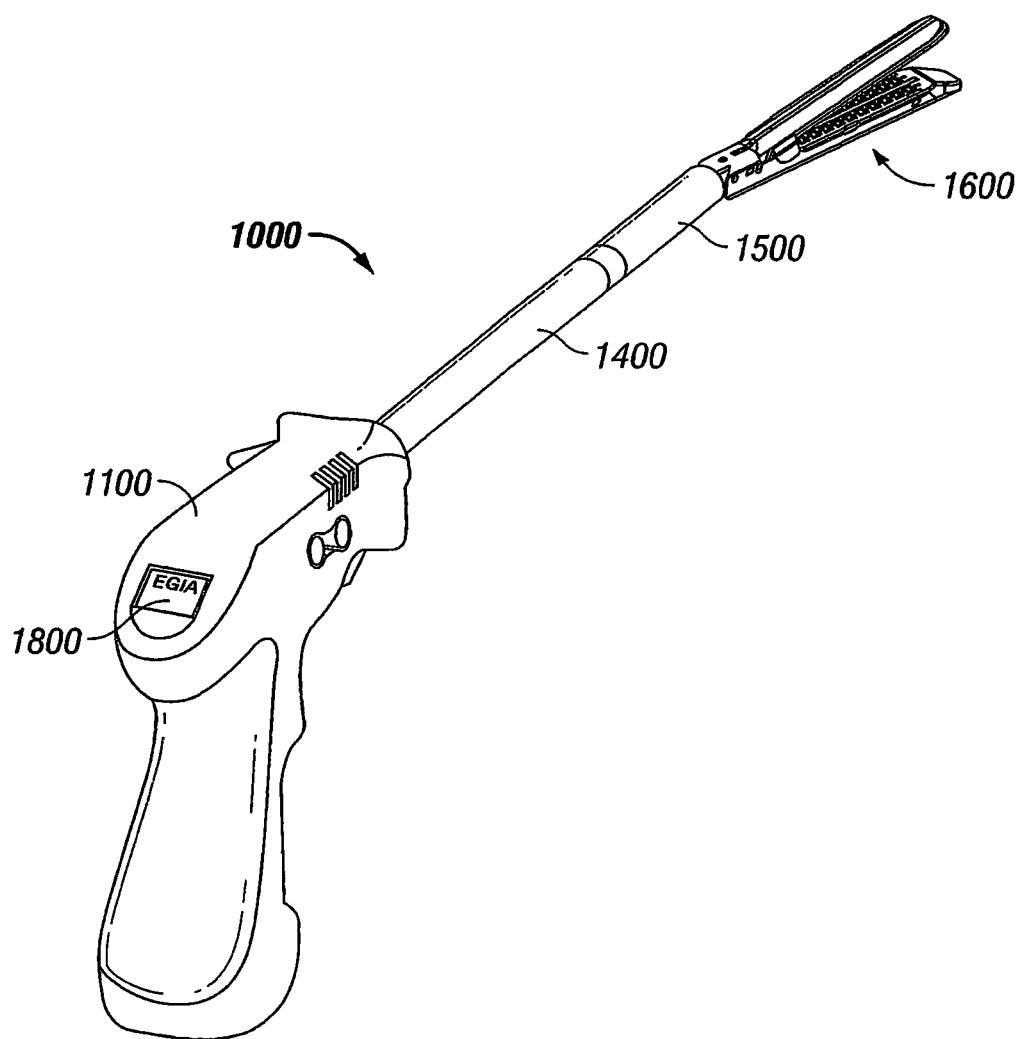
FIG. 19 is a rear perspective view of the powered surgical instrument of FIG. 16.

With continued reference to FIG. 16, endoscopic portion 1400 extends distally from housing 1100, shaft portion 1500 is selectively connectable to a distal end 1402 of endoscopic portion 1400 and end effector 1600 is selectively connectable to an end 1502 of shaft portion 1500. As shown in FIGS. 16-18, a plurality of different shaft portions 1500 may be used with surgical instrument 1000 and a plurality of different end effectors 1600 may also be used with surgical instrument 1000.

More specifically, a plurality of different shaft portions 1500 may be removably connectable to endoscopic portion 1400, e.g., for a particular purpose. It is envisioned that at least a portion of shaft portion 1500 may be articulatable (FIG. 17 A), curved (FIG. 17B) or made from a compliant material (for example, as illustrated in FIG. 17C).

As shown in FIGS. 16-18, a plurality of different classes of end effectors 1600 may be removably connectable to shaft portion 1500 of surgical instrument 1000. It is envisioned that classes of end effectors 1600 that are selectively connectable to distal end 1502 of shaft portion 1600 include those having a pivotable cartridge assembly (FIGS. 16 and 19), a substantially circular cartridge assembly (FIGS. 17 A, 17B and 17C) and parallel jaw members (FIG. 18). It is further envisioned that different sub-classes of each class of end effector 1600 may be connectable to shaft portion 1500.

For instance, within the class of end effectors 1600 including a substantially circular cartridge assembly, sub-classes of such end effectors 1600 include gastrointestinal anastomosis-type devices, transverse anastomosis-type devices (see, e.g. U.S. Pat. Nos. 4,520,817 and 4,383,634) and circular anastomosis-type devices (see, e.g., U.S. Pat. No. 4,304,236). Gastrointestinal anastomosis-type devices are configured to drive and bend staples aligned in a row sequentially in rapid sequence, while transverse anastomosis-type devices drive and bend all staples simultaneously. Circular anastomosis-type devices are configured to simultaneously apply annular rows of staples to tissue.

Additionally, within the class of end effectors 1600 having a pivotable cartridge assembly, sub-classes may include end effectors 1600 configured to drive staples sequentially and end effectors 1600 configured to drive staples simultaneously.

It is therefore envisioned that a particular shaft portion 1500 may be configured for use with a particular class of end effectors 1600, such as end effectors 1600 including a substantially circular cartridge assembly. In such an embodiment, another shaft portion 1500 may be configured for use with another particular class of end effectors 1600, such as end effectors 1600 including a pivotable cartridge assembly or end effectors 1600 having parallel jaw members.

It is further envisioned that a particular shaft portion 1500 may be configured for use with a particular type of end effector 1600, such as end effectors 1600 configured for sequential firing of staples (including end effectors 1600 including a substantially circular cartridge assembly, end effectors 1600 including a pivotable cartridge assembly or end effectors 1600 having parallel jaw members) or end effectors 1600 configured for sequential firing of staples, for example.

Additionally, it is envisioned that a particular shaft portion 1500 may be configured for use with several types of end effectors 1600, including end effectors 1600 including a substantially circular cartridge assembly, a pivotable cartridge assembly, parallel jaw members, configured for sequential firing of staples and/or configured for sequential firing of staples. Here, a physician may select a particular shaft portion 1500 based on other characteristics, such as shaft portion 1500 being articulatable, curved, or compliant, for example.

At least one sensor 1700 may also be included on a portion of surgical instrument 1000. It is envisioned that a first sensor 1700a is included on endoscopic portion 1400, a second sensor 1700b is included on shaft portion 1500, and a third sensor 1700c is included on end effector 1600. It is envisioned that sensors 1700 cooperate with each other for various purposes. For instance, first sensor 1700a may be configured to detect the type of shaft portion 1500 that is engaged with endoscopic portion 1400 (e.g., by communicating with second sensor 1700b). Further, second sensor 1700b may be configured to detect the type of end effector 1600 that is engaged with shaft portion 1500 (e.g., by communicating with third sensor 1700c).

It is further envisioned that a user interface 1800 on housing 1100 is included. In a disclosed embodiment, user interface 1800 includes a screen that displays at least some of the information (e.g., type of shaft portion 1500 connected to endoscopic portion 1400, type of end effector 1600 connected to shaft portion 1500, etc.) detected by sensors 1700 in surgical instrument 1000. User interface 1800 may also display a condition of end effector 1600, such as angle of articulation or rotation, whether staples have been fired therefrom, if tissue is between jaw members, etc. This information may also be provided to a video screen or monitoring system in an operating room. For instance, the data may be transmitted to a receiver for the operating room monitoring system from a communication transmitter incorporated in or associated with powered surgical instrument 1000, via technology including Blue Tooth, ANT3, KNX, Z Wave, XI0, wireless USB, WiFi, IrDa, Nanonet, Tiny OS, ZigBee, radio, UHF and VHF.

The present disclosure also relates to a method of applying surgical fasteners to tissue. The method includes the step of providing a powered surgical instrument 100, 1000, as described above. The method also includes connecting shaft portion 1500 to distal end 1402 of endoscopic portion 1400 and connecting end effector 1600 to distal end 1502 of shaft portion 1500.

It will be understood that various modifications may be made to the embodiments disclosed herein. For example, the locations along the longitudinal axis for drive motor 210 and/or drive gear 200 may be different than shown. Different types of gears for driving, rotation, articulation and/or actuation may be used. Therefore, the above description should not be construed as limiting, but merely as exemplifications of various embodiments. Those skilled in the art will envision other modifications within the scope and spirit of the claims appended hereto.

The invention claimed is:

1. A transmission for a surgical tool, the transmission comprising:
   a housing;
   a first actuator configured to rotate an end effector of the surgical tool;
   a second actuator configured to move a first jaw of an end effector of the surgical tool relative to a second jaw of the end effector of the surgical tool;
   a first input disposed at least partially within the housing; and
   a second input disposed at least partially within the housing, the second input moveable between a first position in which the first input is engaged with the first actuator and a second position in which the first input is disengaged from the first actuator and the first input is engaged with the second actuator.

2. The transmission of claim 1, wherein the second input defines a first axis and the second input is rotatable about the first axis to move the second input between the first position and the second position.

3. The transmission of claim 1, wherein the first actuator includes a first gear and the second actuator includes a second gear.

4. The transmission of claim 1, further including a third actuator configured to eject staples from the end effector.

5. The transmission of claim 4, wherein the second input is moveable to a third position in which the first input is disengaged from the first and second actuators and the first input is engaged with the third actuator.

6. The transmission of claim 5, wherein the second input is rotatable about the first axis to move the second input to the third position.

7. The transmission of claim 4, wherein the third actuator includes a third gear.

8. A surgical system comprising:
   the transmission of claim 1;
   a first motor configured to rotate the first input; and
   a second motor configured to rotate the second input.

9. The surgical system of claim 8, further comprising:
   a shaft having a proximal end and a distal end, the proximal end of the shaft being connected to the housing; and
   a loading unit removably coupled to the distal end of the shaft, the loading unit comprising the end effector at a distal end of the loading unit, the end effector having the first jaw and the second jaw.

10. A surgical system comprising:
    a surgical tool including,
    a housing;
    a first actuator configured to rotate an end effector of the surgical tool;
    a second actuator configured to move a first jaw of an end effector of the surgical tool relative to a second jaw of the end effector of the surgical tool;
    a first input disposed at least partially within the housing; and
    a second input disposed at least partially within the housing, the second input moveable between a first position in which the first input is engaged with the first actuator and a second position in which the first input is disengaged from the first actuator and the first input is engaged with the second actuator;
    a first motor configured to rotate the first input; and
    a second motor configured to rotate the second input.

11. The surgical system of claim 10, wherein the second input defines a first axis and the second input is rotatable about the first axis to move the second input between the first position and the second position.

12. The surgical system of claim 10, wherein the first actuator includes a first gear and the second actuator includes a second gear.

13. The surgical system of claim 10, further including:
    a tool shaft having a proximal end and a distal end, the proximal end of the tool shaft being connected to the housing; and
    a loading unit removably coupled to the distal end of the tool shaft, the loading unit comprising the end effector at a distal end of the loading unit, the end effector having the first jaw and the second jaw.

14. The surgical system of claim 10, further including a third actuator configured to eject staples from the end effector.

15. The surgical system of claim 14 wherein the second input is moveable to a third position in which the first input is disengaged from the first actuator and the second actuator and the first input is engaged with the third actuator.

16. The surgical system of claim 15, wherein the second input is rotatable about the first axis to move the second input to the third position.

17. The surgical system of claim 16, wherein the third actuator includes a third gear.

18. A surgical system comprising:
    a surgical tool including:
    a housing;
    a shaft having a proximal end and a distal end, the proximal end of the tool shaft being connected to the housing;
    a loading unit removably coupled to the distal end of the tool shaft, the loading unit comprising an end effector at a distal end of the loading unit, the end effector having a first jaw and a second jaw;
    a first actuator configured to rotate the end effector, the first actuator including a first gear;
    a second actuator configured to move the first jaw of the end effector relative to the second jaw of the end effector, the second actuator including a second gear;
    a first input disposed at least partially within the housing; and a second input disposed at least partially within the housing, the second input moveable between a first position in which the first input is engaged with the first actuator and a second position in which the first input is disengaged from the first actuator and the first input is engaged with the second actuator, wherein the second input defines a first axis and the second input is rotatable about the first axis to move the second input between the first position and the second position.

19. The surgical system of claim 18, further including a first motor configured to rotate the first input.

20. The surgical system of claim 19, further including a second motor configured to rotate the second input.

* * * * *